(12) United States Patent
Howell et al.

(10) Patent No.: US 11,819,638 B2
(45) Date of Patent: Nov. 21, 2023

(54) RAPIDLY INSERTABLE CENTRAL CATHETERS INCLUDING CATHETER ASSEMBLIES AND METHODS THEREOF

(71) Applicant: Bard Access Systems, Inc., Salt Lake City, UT (US)

(72) Inventors: Glade H. Howell, Draper, UT (US); Jason R. Stats, Layton, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 96 days.

(21) Appl. No.: 17/326,017

(22) Filed: May 20, 2021

(65) Prior Publication Data

US 2021/0361915 A1 Nov. 25, 2021

Related U.S. Application Data

(60) Provisional application No. 63/028,445, filed on May 21, 2020.

(51) Int. Cl.
*A61M 25/06* (2006.01)
*A61M 25/00* (2006.01)
(Continued)

(52) U.S. Cl.
CPC ...... *A61M 25/0631* (2013.01); *A61M 25/007* (2013.01); *A61M 25/0026* (2013.01);
(Continued)

(58) Field of Classification Search
CPC ............. A61M 25/09; A61M 25/0631; A61M 25/0026; A61M 25/007; A61M 25/0693;
(Continued)

(56) References Cited

U.S. PATENT DOCUMENTS 1,013,691 A 1/1912 Shields
3,225,762 A 12/1965 Guttman
(Continued)

FOREIGN PATENT DOCUMENTS

DE 202012006191 U1 7/2012
EP 0653220 A1 5/1995
(Continued)

OTHER PUBLICATIONS

PCT/US2021/014700 filed Jan. 22, 2021 International Search Report and Written Opinion dated Jun. 29, 2021.
(Continued)

*Primary Examiner* — Brandy S Lee
*Assistant Examiner* — Kathleen Paige Farrell
(74) *Attorney, Agent, or Firm* — Rutan & Tucker LLP

(57) ABSTRACT

Rapidly insertable central catheters ("RICCs") including catheter assemblies and methods thereof are disclosed. For example, a RICC assembly includes a RICC and an introducer. The RICC includes a catheter tube, a catheter hub, and one or more extension legs coupled in the foregoing order. The catheter tube includes a side aperture that opens into an introducing lumen that extends from at least the side aperture to a distal end of the RICC. The introducer includes a retractable-needle device, a syringe, and a coupling hub that couples the retractable-needle device and the syringe together proximal of the side aperture in a ready-to-deploy state of the RICC assembly. The retractable-needle device includes an introducer needle. A needle tip in a distal-end portion of a shaft of the introducer needle extends beyond the distal end of the RICC when the RICC assembly is in the ready-to-deploy state of the RICC assembly.

23 Claims, 9 Drawing Sheets

(51) Int. Cl.
*A61M 25/09* (2006.01)
*A61M 25/02* (2006.01)

(52) U.S. Cl.
CPC .... *A61M 25/0097* (2013.01); *A61M 25/0606* (2013.01); *A61M 25/0693* (2013.01); *A61M 25/09* (2013.01); *A61M 25/09041* (2013.01); *A61M 25/001* (2013.01); *A61M 2025/024* (2013.01); *A61M 2025/0687* (2013.01)

(58) Field of Classification Search
CPC ........ A61M 2025/024; A61M 25/0097; A61M 2025/0687; A61M 25/09041; A61M 25/0606
See application file for complete search history.

(56) References Cited

U.S. PATENT DOCUMENTS

| | | |
|---|---|---|
| 3,382,872 A | 5/1968 | Rubin |
| 3,570,485 A | 3/1971 | Reilly |
| 3,890,976 A | 6/1975 | Bazell et al. |
| 4,205,675 A | 6/1980 | Vaillancourt |
| 4,292,970 A | 10/1981 | Hession, Jr. |
| 4,468,224 A | 8/1984 | Enzmann et al. |
| 4,525,157 A | 6/1985 | Vaillancourt |
| 4,581,019 A | 4/1986 | Curelaru et al. |
| 4,594,073 A | 6/1986 | Stine |
| 4,702,735 A | 10/1987 | Luther et al. |
| 4,743,265 A | 5/1988 | Whitehouse et al. |
| 4,766,908 A | 8/1988 | Clement |
| 4,863,432 A | 9/1989 | Kvalo |
| 4,950,252 A | 8/1990 | Luther et al. |
| 4,994,040 A | 2/1991 | Cameron et al. |
| 5,017,259 A | 5/1991 | Kohsai |
| 5,040,548 A | 8/1991 | Yock |
| 5,057,073 A | 10/1991 | Martin |
| 5,112,312 A | 5/1992 | Luther |
| 5,115,816 A | 5/1992 | Lee |
| 5,120,317 A | 6/1992 | Luther |
| 5,158,544 A | 10/1992 | Weinstein |
| 5,188,593 A | 2/1993 | Martin |
| 5,195,962 A | 3/1993 | Martin et al. |
| 5,207,650 A | 5/1993 | Martin |
| 5,267,958 A | 12/1993 | Buchbinder et al. |
| 5,295,970 A | 3/1994 | Clinton et al. |
| 5,306,247 A | 4/1994 | Pfenninger |
| 5,322,512 A | 6/1994 | Mohiuddin |
| 5,328,472 A | 7/1994 | Steinke et al. |
| 5,350,358 A | 9/1994 | Martin |
| 5,358,495 A | 10/1994 | Lynn |
| 5,368,567 A | 11/1994 | Lee |
| 5,378,230 A | 1/1995 | Mahurkar |
| 5,380,290 A | 1/1995 | Makower et al. |
| 5,389,087 A | 2/1995 | Miraki |
| 5,439,449 A | 8/1995 | Mapes et al. |
| 5,443,457 A | 8/1995 | Ginn et al. |
| 5,460,185 A | 10/1995 | Johnson et al. |
| 5,489,271 A | 2/1996 | Andersen |
| 5,573,520 A | 11/1996 | Schwartz et al. |
| 5,683,370 A | 11/1997 | Luther et al. |
| 5,718,678 A | 2/1998 | Fleming, III |
| 5,772,636 A | 6/1998 | Brimhall et al. |
| 5,885,251 A | 3/1999 | Luther |
| 5,919,164 A | 7/1999 | Andersen |
| 5,921,971 A | 7/1999 | Agro et al. |
| 5,947,940 A | 9/1999 | Beisel |
| 5,957,893 A | 9/1999 | Luther et al. |
| 5,971,957 A | 10/1999 | Luther et al. |
| 6,159,198 A | 12/2000 | Gardeski et al. |
| 6,206,849 B1 | 3/2001 | Martin et al. |
| 6,228,062 B1 | 5/2001 | Howell et al. |
| 6,475,187 B1 | 11/2002 | Gerberding |
| 6,606,515 B1 | 8/2003 | Windheuser et al. |
| 6,626,869 B1 | 9/2003 | Bint |
| 6,716,228 B2 | 4/2004 | Tal |
| 6,726,659 B1 | 4/2004 | Stocking et al. |
| 6,819,951 B2 | 11/2004 | Patel et al. |
| 6,821,287 B1 | 11/2004 | Jang |
| 6,926,692 B2 | 8/2005 | Katoh et al. |
| 6,962,575 B2 | 11/2005 | Tal |
| 6,991,625 B1 | 1/2006 | Gately et al. |
| 6,994,693 B2 | 2/2006 | Tal |
| 6,999,809 B2 | 2/2006 | Currier et al. |
| 7,025,746 B2 | 4/2006 | Tal |
| 7,029,467 B2 | 4/2006 | Currier et al. |
| 7,037,293 B2 | 5/2006 | Carrillo et al. |
| 7,074,231 B2 | 7/2006 | Jang |
| 7,141,050 B2 | 11/2006 | Deal et al. |
| 7,144,386 B2 | 12/2006 | Korkor et al. |
| 7,311,697 B2 | 12/2007 | Osborne |
| 7,364,566 B2 | 4/2008 | Elkins et al. |
| 7,377,910 B2 | 5/2008 | Katoh et al. |
| 7,390,323 B2 | 6/2008 | Jang |
| D600,793 S | 9/2009 | Bierman et al. |
| D601,242 S | 9/2009 | Bierman et al. |
| D601,243 S | 9/2009 | Bierman et al. |
| 7,594,911 B2 | 9/2009 | Powers et al. |
| 7,691,093 B2 | 4/2010 | Brimhall |
| 7,722,567 B2 | 5/2010 | Tal |
| D617,893 S | 6/2010 | Bierman et al. |
| D624,643 S | 9/2010 | Bierman et al. |
| 7,819,889 B2 | 10/2010 | Healy et al. |
| 7,857,788 B2 | 12/2010 | Racz |
| D630,729 S | 1/2011 | Bierman et al. |
| 7,909,797 B2 | 3/2011 | Kennedy, II et al. |
| 7,909,811 B2 | 3/2011 | Agro et al. |
| 7,922,696 B2 | 4/2011 | Tal et al. |
| 7,938,820 B2 | 5/2011 | Webster et al. |
| 7,967,834 B2 | 6/2011 | Tal et al. |
| 7,976,511 B2 | 7/2011 | Fojtik |
| 7,985,204 B2 | 7/2011 | Katoh et al. |
| 8,073,517 B1 | 12/2011 | Burchman |
| 8,105,286 B2 | 1/2012 | Anderson et al. |
| 8,192,402 B2 | 6/2012 | Anderson et al. |
| 8,202,251 B2 | 6/2012 | Bierman et al. |
| 8,206,356 B2 | 6/2012 | Katoh et al. |
| 8,361,011 B2 | 1/2013 | Mendels |
| 8,372,107 B2 | 2/2013 | Tupper |
| 8,377,006 B2 | 2/2013 | Tal et al. |
| 8,454,577 B2 | 6/2013 | Joergensen et al. |
| 8,585,858 B2 | 11/2013 | Kronfeld et al. |
| 8,657,790 B2 | 2/2014 | Tal et al. |
| 8,672,888 B2 | 3/2014 | Tal |
| 8,696,645 B2 | 4/2014 | Tal et al. |
| 8,784,362 B2 | 7/2014 | Boutilette et al. |
| 8,827,958 B2 | 9/2014 | Bierman et al. |
| 8,876,704 B2 | 11/2014 | Golden et al. |
| 8,882,713 B1 | 11/2014 | Call et al. |
| 8,900,192 B2 | 12/2014 | Anderson et al. |
| 8,900,207 B2 | 12/2014 | Uretsky |
| 8,915,884 B2 | 12/2014 | Tal et al. |
| 8,956,327 B2 | 2/2015 | Bierman et al. |
| 9,023,093 B2 | 5/2015 | Pal |
| 9,126,012 B2 | 9/2015 | McKinnon et al. |
| 9,138,252 B2 | 9/2015 | Bierman et al. |
| 9,180,275 B2 | 11/2015 | Helm |
| 9,265,920 B2 | 2/2016 | Rundquist et al. |
| 9,272,121 B2 | 3/2016 | Piccagli |
| 9,445,734 B2 | 9/2016 | Grunwald |
| 9,522,254 B2 | 12/2016 | Belson |
| 9,554,785 B2 | 1/2017 | Walters et al. |
| 9,566,087 B2 | 2/2017 | Bierman et al. |
| 9,675,784 B2 | 6/2017 | Belson |
| 9,713,695 B2 | 7/2017 | Bunch et al. |
| 9,764,117 B2 | 9/2017 | Bierman et al. |
| 9,770,573 B2 | 9/2017 | Golden et al. |
| 9,814,861 B2 | 11/2017 | Boutilette et al. |
| 9,820,845 B2 | 11/2017 | von Lehe et al. |
| 9,861,383 B2 | 1/2018 | Clark |
| 9,872,971 B2 | 1/2018 | Blanchard |
| 9,884,169 B2 | 2/2018 | Bierman et al. |
| 9,889,275 B2 | 2/2018 | Voss et al. |
| 9,913,585 B2 | 3/2018 | McCaffrey et al. |
| 9,913,962 B2 | 3/2018 | Tal et al. |

(56) References Cited

U.S. PATENT DOCUMENTS

| | | |
|---|---|---|
| 9,981,113 B2 | 5/2018 | Bierman |
| 10,010,312 B2 | 7/2018 | Tegels |
| 10,065,020 B2 | 9/2018 | Gaur |
| 10,086,170 B2 * | 10/2018 | Chhikara et al. .. A61M 25/0606 |
| 10,098,724 B2 | 10/2018 | Adams et al. |
| 10,111,683 B2 | 10/2018 | Tsamir et al. |
| 10,118,020 B2 | 11/2018 | Avneri et al. |
| 10,130,269 B2 | 11/2018 | McCaffrey et al. |
| 10,220,184 B2 | 3/2019 | Clark |
| 10,220,191 B2 | 3/2019 | Belson et al. |
| 10,265,508 B2 | 4/2019 | Baid |
| 10,271,873 B2 | 4/2019 | Steingisser et al. |
| 10,376,675 B2 | 8/2019 | Mitchell et al. |
| 10,675,440 B2 | 6/2020 | Abitabilo et al. |
| 10,806,901 B2 | 10/2020 | Burkholz et al. |
| 10,926,060 B2 | 2/2021 | Stern et al. |
| 2002/0040231 A1 | 4/2002 | Wysoki |
| 2002/0198492 A1 | 12/2002 | Miller et al. |
| 2003/0036712 A1 | 2/2003 | Heh et al. |
| 2003/0060863 A1 | 3/2003 | Dobak |
| 2003/0088212 A1 | 5/2003 | Tal |
| 2003/0100849 A1 | 5/2003 | Jang |
| 2003/0153874 A1 | 8/2003 | Tal |
| 2003/0158514 A1 | 8/2003 | Tal |
| 2004/0015138 A1 | 1/2004 | Currier et al. |
| 2004/0064086 A1 | 4/2004 | Gottlieb et al. |
| 2004/0116864 A1 | 6/2004 | Boudreaux |
| 2004/0116901 A1 | 6/2004 | Appling |
| 2004/0167478 A1 | 8/2004 | Mooney et al. |
| 2004/0193093 A1 | 9/2004 | Desmond |
| 2004/0230178 A1 | 11/2004 | Wu |
| 2005/0004554 A1 | 1/2005 | Osborne |
| 2005/0120523 A1 | 6/2005 | Schweikert |
| 2005/0131343 A1 | 6/2005 | Abrams et al. |
| 2005/0215956 A1 | 9/2005 | Nerney |
| 2005/0245882 A1 | 11/2005 | Elkins et al. |
| 2005/0283221 A1 | 12/2005 | Mann et al. |
| 2006/0009740 A1 | 1/2006 | Higgins et al. |
| 2006/0116629 A1 | 6/2006 | Tal et al. |
| 2006/0129100 A1 | 6/2006 | Tal |
| 2006/0129130 A1 | 6/2006 | Tal et al. |
| 2007/0276288 A1 | 11/2007 | Khaw |
| 2008/0045894 A1 | 2/2008 | Perchik et al. |
| 2008/0125744 A1 | 5/2008 | Treacy |
| 2008/0125748 A1 | 5/2008 | Patel |
| 2008/0132850 A1 | 6/2008 | Fumiyama et al. |
| 2008/0262430 A1 | 10/2008 | Anderson et al. |
| 2008/0262431 A1 | 10/2008 | Anderson et al. |
| 2008/0294111 A1 | 11/2008 | Tal et al. |
| 2008/0312578 A1 | 12/2008 | DeFonzo et al. |
| 2008/0319387 A1 | 12/2008 | Amisar et al. |
| 2009/0187147 A1 | 7/2009 | Kurth et al. |
| 2009/0221961 A1 | 9/2009 | Tal et al. |
| 2009/0270889 A1 | 10/2009 | Tal et al. |
| 2010/0030154 A1 | 2/2010 | Duffy |
| 2010/0256487 A1 | 10/2010 | Hawkins et al. |
| 2010/0298839 A1 | 11/2010 | Castro |
| 2010/0305474 A1 | 12/2010 | DeMars et al. |
| 2011/0004162 A1 | 1/2011 | Tal |
| 2011/0009827 A1 | 1/2011 | Bierman et al. |
| 2011/0021994 A1 | 1/2011 | Anderson et al. |
| 2011/0066142 A1 | 3/2011 | Tal et al. |
| 2011/0071502 A1 * | 3/2011 | Asai ............... A61M 25/09041 604/528 |
| 2011/0144620 A1 | 6/2011 | Tal |
| 2011/0152836 A1 | 6/2011 | Riopelle et al. |
| 2011/0202006 A1 | 8/2011 | Bierman et al. |
| 2011/0251559 A1 | 10/2011 | Tal et al. |
| 2011/0270192 A1 | 11/2011 | Anderson et al. |
| 2012/0041371 A1 | 2/2012 | Tal et al. |
| 2012/0065590 A1 | 3/2012 | Bierman et al. |
| 2012/0078231 A1 | 3/2012 | Hoshinouchi |
| 2012/0130411 A1 | 5/2012 | Tal et al. |
| 2012/0130415 A1 | 5/2012 | Tal et al. |
| 2012/0157854 A1 | 6/2012 | Kumis et al. |
| 2012/0215171 A1 | 8/2012 | Christiansen |
| 2012/0220942 A1 | 8/2012 | Hall et al. |
| 2012/0283640 A1 | 11/2012 | Anderson et al. |
| 2012/0316500 A1 | 12/2012 | Bierman et al. |
| 2013/0053763 A1 | 2/2013 | Makino et al. |
| 2013/0053826 A1 | 2/2013 | Shevgoor |
| 2013/0123704 A1 | 5/2013 | Bierman et al. |
| 2013/0158338 A1 | 6/2013 | Kelly et al. |
| 2013/0188291 A1 | 7/2013 | Vardiman |
| 2013/0237931 A1 | 9/2013 | Tal et al. |
| 2013/0306079 A1 | 11/2013 | Tracy |
| 2014/0025036 A1 | 1/2014 | Bierman et al. |
| 2014/0081210 A1 | 3/2014 | Bierman et al. |
| 2014/0100552 A1 | 4/2014 | Gallacher et al. |
| 2014/0207052 A1 | 7/2014 | Tal et al. |
| 2014/0207069 A1 | 7/2014 | Bierman et al. |
| 2014/0214005 A1 | 7/2014 | Belson |
| 2014/0257111 A1 | 9/2014 | Yamashita et al. |
| 2014/0276432 A1 | 9/2014 | Bierman et al. |
| 2014/0276599 A1 | 9/2014 | Cully et al. |
| 2015/0080939 A1 | 3/2015 | Adams et al. |
| 2015/0094653 A1 | 4/2015 | Pacheco et al. |
| 2015/0112310 A1 | 4/2015 | Call et al. |
| 2015/0126930 A1 | 5/2015 | Bierman et al. |
| 2015/0148595 A1 | 5/2015 | Bagwell et al. |
| 2015/0190168 A1 | 7/2015 | Bierman et al. |
| 2015/0196210 A1 | 7/2015 | McCaffrey et al. |
| 2015/0224287 A1 | 8/2015 | Bian et al. |
| 2015/0283357 A1 | 10/2015 | Lampropoulos et al. |
| 2015/0297868 A1 | 10/2015 | Tal et al. |
| 2015/0320969 A1 | 11/2015 | Haslinger et al. |
| 2015/0320977 A1 | 11/2015 | Vitullo et al. |
| 2015/0351793 A1 | 12/2015 | Bierman et al. |
| 2015/0359549 A1 | 12/2015 | Lenker et al. |
| 2015/0359998 A1 | 12/2015 | Carmel et al. |
| 2016/0082223 A1 | 3/2016 | Barnell |
| 2016/0114124 A1 | 4/2016 | Tal |
| 2016/0158523 A1 | 6/2016 | Helm |
| 2016/0220786 A1 | 8/2016 | Mitchell et al. |
| 2016/0325073 A1 | 11/2016 | Davies et al. |
| 2016/0338728 A1 | 11/2016 | Tal |
| 2016/0346503 A1 | 12/2016 | Jackson et al. |
| 2017/0035990 A1 | 2/2017 | Swift |
| 2017/0072165 A1 | 3/2017 | Lim et al. |
| 2017/0120000 A1 | 5/2017 | Osypka et al. |
| 2017/0120014 A1 | 5/2017 | Harding et al. |
| 2017/0120034 A1 | 5/2017 | Kaczorowski |
| 2017/0128700 A1 | 5/2017 | Roche Rebollo |
| 2017/0156987 A1 | 6/2017 | Babbs et al. |
| 2017/0172653 A1 | 6/2017 | Urbanski et al. |
| 2017/0239443 A1 | 8/2017 | Abitabilo et al. |
| 2017/0259043 A1 | 9/2017 | Chan et al. |
| 2017/0273713 A1 | 9/2017 | Shah et al. |
| 2017/0326339 A1 | 11/2017 | Bailey et al. |
| 2017/0361070 A1 | 12/2017 | Hivert |
| 2017/0368255 A1 | 12/2017 | Provost et al. |
| 2018/0021545 A1 | 1/2018 | Mitchell et al. |
| 2018/0116690 A1 | 5/2018 | Sarabia et al. |
| 2018/0117284 A1 | 5/2018 | Appling et al. |
| 2018/0133438 A1 | 5/2018 | Hulvershorn et al. |
| 2018/0154062 A1 | 6/2018 | DeFonzo et al. |
| 2018/0154112 A1 | 6/2018 | Chan et al. |
| 2018/0214674 A1 | 8/2018 | Ebnet et al. |
| 2018/0296799 A1 | 10/2018 | Horst et al. |
| 2018/0296804 A1 | 10/2018 | Bierman |
| 2018/0310955 A1 | 11/2018 | Lindekugel et al. |
| 2019/0015646 A1 | 1/2019 | Matlock et al. |
| 2019/0060616 A1 | 2/2019 | Solomon |
| 2019/0076167 A1 | 3/2019 | Fantuzzi et al. |
| 2019/0134349 A1 | 5/2019 | Cohn et al. |
| 2019/0192824 A1 | 6/2019 | Cordeiro et al. |
| 2019/0201665 A1 | 7/2019 | Turpin |
| 2019/0209812 A1 * | 7/2019 | Burkholz et al. .. A61M 25/0606 |
| 2019/0255294 A1 | 8/2019 | Mitchell et al. |
| 2019/0255298 A1 | 8/2019 | Mitchell et al. |
| 2019/0275303 A1 | 9/2019 | Tran et al. |
| 2019/0276268 A1 | 9/2019 | Akingba |
| 2019/0321590 A1 | 10/2019 | Burkholz et al. |
| 2020/0001051 A1 | 1/2020 | Huang et al. |

(56) References Cited

U.S. PATENT DOCUMENTS

| | | | |
|---|---|---|---|
| 2020/0016374 A1 | 1/2020 | Burkholz et al. | |
| 2020/0046948 A1 | 2/2020 | Burkholz et al. | |
| 2020/0100716 A1* | 4/2020 | Devgon et al. | A61B 5/15003 |
| 2020/0129732 A1 | 4/2020 | Vogt et al. | |
| 2020/0147349 A1 | 5/2020 | Holt | |
| 2020/0197684 A1 | 6/2020 | Wax | |
| 2020/0237278 A1 | 7/2020 | Asbaghi | |
| 2020/0359995 A1 | 11/2020 | Walsh et al. | |
| 2021/0030944 A1 | 2/2021 | Cushen et al. | |
| 2021/0069471 A1 | 3/2021 | Howell | |
| 2021/0085927 A1 | 3/2021 | Howell | |
| 2021/0100985 A1 | 4/2021 | Akcay et al. | |
| 2021/0113809 A1 | 4/2021 | Howell | |
| 2021/0113810 A1 | 4/2021 | Howell | |
| 2021/0113816 A1 | 4/2021 | DiCianni | |
| 2021/0121661 A1 | 4/2021 | Howell | |
| 2021/0121667 A1 | 4/2021 | Howell | |
| 2021/0228842 A1 | 7/2021 | Scherich et al. | |
| 2021/0228843 A1 | 7/2021 | Howell et al. | |
| 2021/0290898 A1 | 9/2021 | Burkholz | |
| 2021/0290901 A1 | 9/2021 | Burkholz et al. | |
| 2021/0290913 A1* | 9/2021 | Horst et al. | A61M 25/0631 |
| 2021/0322729 A1 | 10/2021 | Howell | |
| 2021/0330941 A1* | 10/2021 | Howell et al. | A61M 25/0631 |
| 2021/0330942 A1 | 10/2021 | Howell | |
| 2021/0402149 A1 | 12/2021 | Howell | |
| 2021/0402153 A1 | 12/2021 | Howell et al. | |
| 2022/0001138 A1 | 1/2022 | Howell | |
| 2022/0032013 A1 | 2/2022 | Howell et al. | |
| 2022/0032014 A1 | 2/2022 | Howell et al. | |
| 2022/0062528 A1 | 3/2022 | Thornley et al. | |
| 2022/0126064 A1 | 4/2022 | Tobin et al. | |
| 2022/0193376 A1 | 6/2022 | Spataro et al. | |
| 2022/0193377 A1 | 6/2022 | Haymond et al. | |
| 2022/0193378 A1 | 6/2022 | Spataro et al. | |
| 2022/0323723 A1 | 10/2022 | Spataro et al. | |
| 2022/0331563 A1* | 10/2022 | Papadia | A61M 39/06 |
| 2023/0042898 A1 | 2/2023 | Howell et al. | |
| 2023/0096377 A1 | 3/2023 | West et al. | |
| 2023/0096740 A1 | 3/2023 | Bechstein et al. | |
| 2023/0099654 A1 | 3/2023 | Blanchard et al. | |
| 2023/0100482 A1 | 3/2023 | Howell | |
| 2023/0101455 A1 | 3/2023 | Howell et al. | |
| 2023/0102231 A1 | 3/2023 | Bechstein et al. | |
| 2023/0233814 A1 | 7/2023 | Howell et al. | |

FOREIGN PATENT DOCUMENTS

| | | |
|---|---|---|
| EP | 0730880 A1 | 9/1996 |
| EP | 2061385 A1 | 5/2009 |
| EP | 1458437 B1 | 3/2010 |
| EP | 2248549 A2 | 11/2010 |
| EP | 2319576 A1 | 5/2011 |
| EP | 2366422 A1 | 9/2011 |
| EP | 2486880 A2 | 8/2012 |
| EP | 2486881 A2 | 8/2012 |
| EP | 2486951 A2 | 8/2012 |
| EP | 2512576 A2 | 10/2012 |
| EP | 2152348 B1 | 2/2015 |
| EP | 3473291 A1 | 4/2019 |
| EP | 3093038 B1 | 5/2019 |
| EP | 2260897 B1 | 9/2019 |
| EP | 3693051 A1 | 8/2020 |
| GB | 1273547 A | 5/1972 |
| JP | 2004248987 A | 9/2004 |
| JP | 2008054859 A | 3/2008 |
| WO | 94/21315 A1 | 9/1994 |
| WO | 95/32009 A2 | 11/1995 |
| WO | 98/44979 A1 | 10/1998 |
| WO | 98/53871 A1 | 12/1998 |
| WO | 99/12600 A1 | 3/1999 |
| WO | 99/26681 A1 | 6/1999 |
| WO | 00/06221 A1 | 2/2000 |
| WO | 2003008020 A1 | 1/2003 |
| WO | 2003057272 A2 | 7/2003 |
| WO | 03/068073 A1 | 8/2003 |
| WO | 2003066125 A2 | 8/2003 |
| WO | 2005/096778 A2 | 10/2005 |
| WO | 2006055288 A2 | 5/2006 |
| WO | 2006055780 A2 | 5/2006 |
| WO | 2007046850 A2 | 4/2007 |
| WO | 2008033983 A1 | 3/2008 |
| WO | 2008092029 A2 | 7/2008 |
| WO | 2008/131300 A2 | 10/2008 |
| WO | 2008131289 A2 | 10/2008 |
| WO | 2009114833 A1 | 9/2009 |
| WO | 2009114837 A2 | 9/2009 |
| WO | 2010/048449 A2 | 4/2010 |
| WO | 2010056906 A2 | 5/2010 |
| WO | 2010083467 A2 | 7/2010 |
| WO | 2010/132608 A2 | 11/2010 |
| WO | 2011081859 A2 | 7/2011 |
| WO | 2011097639 A2 | 8/2011 |
| WO | 2011/109792 A1 | 9/2011 |
| WO | 2011146764 A1 | 11/2011 |
| WO | 2012068162 A2 | 5/2012 |
| WO | 2012068166 A2 | 5/2012 |
| WO | 2012135761 A1 | 10/2012 |
| WO | 2012/154277 A1 | 11/2012 |
| WO | 2012162677 A1 | 11/2012 |
| WO | 2013026045 A1 | 2/2013 |
| WO | 2013138519 A1 | 9/2013 |
| WO | 2014006403 A1 | 1/2014 |
| WO | 2014/100392 A1 | 6/2014 |
| WO | 2014113257 A2 | 7/2014 |
| WO | 2014152005 A2 | 9/2014 |
| WO | 2014197614 A2 | 12/2014 |
| WO | 2015057766 A1 | 4/2015 |
| WO | 2015077560 A1 | 5/2015 |
| WO | 2015/168655 A2 | 11/2015 |
| WO | 2016110824 A1 | 7/2016 |
| WO | 2016123278 A1 | 8/2016 |
| WO | 2016139590 A1 | 9/2016 |
| WO | 2016139597 A2 | 9/2016 |
| WO | 2016/178974 A1 | 11/2016 |
| WO | 2016/187063 A1 | 11/2016 |
| WO | 2016176065 A1 | 11/2016 |
| WO | 2018089275 A1 | 5/2018 |
| WO | 2018089285 A1 | 5/2018 |
| WO | 2018089385 A1 | 5/2018 |
| WO | 2018191547 A1 | 10/2018 |
| WO | 2018213148 A1 | 11/2018 |
| WO | 2018218236 A1 | 11/2018 |
| WO | 2019/050576 A1 | 3/2019 |
| WO | 2019/146026 A1 | 8/2019 |
| WO | 2019199734 A1 | 10/2019 |
| WO | 2020014149 A1 | 1/2020 |
| WO | 2020069395 A1 | 4/2020 |
| WO | 2020/109448 A1 | 6/2020 |
| WO | 2020/113123 A1 | 6/2020 |
| WO | 2021050302 A1 | 3/2021 |
| WO | 2021/077103 A1 | 4/2021 |
| WO | 2021062023 A1 | 4/2021 |
| WO | 2021081205 A1 | 4/2021 |
| WO | 2021086793 A1 | 5/2021 |
| WO | 2021/236950 A1 | 11/2021 |
| WO | 2022/031618 A1 | 2/2022 |
| WO | 2022/094141 A1 | 5/2022 |
| WO | 2022/133297 A1 | 6/2022 |
| WO | 2022-140406 A1 | 6/2022 |
| WO | 2022/140429 A1 | 6/2022 |
| WO | 2022/217098 A1 | 10/2022 |
| WO | 2023014994 A1 | 2/2023 |
| WO | 2023049498 A1 | 3/2023 |
| WO | 2023049505 A1 | 3/2023 |
| WO | 2023049511 A1 | 3/2023 |
| WO | 2023049519 A1 | 3/2023 |
| WO | 2023049522 A1 | 3/2023 |

OTHER PUBLICATIONS

PCT/US2021/028018 filed Apr. 19, 2021 International Search Report and Written Opinion dated Sep. 13, 2021.

(56) References Cited

OTHER PUBLICATIONS

PCT/US2021/028683 filed Apr. 22, 2021 International Search Report and Written Opinion dated Sep. 16, 2021.
PCT/US2021/033443 filed May 20, 2021 International Search Report and Written Opinion dated Sep. 23, 2021.
PCT/US2021/029183 filed Apr. 26, 2021 International Search Report and Written Opinion dated Sep. 24, 2021.
PCT/US2021/039843 filed Jun. 30, 2021 International Search Report and Written Opinion dated Nov. 11, 2021.
PCT/US2021/044029 filed Jul. 30, 2021 International Search Report and Written Opinion dated Dec. 9, 2021.
PCT/US2020/048583 filed Aug. 28, 2020 International Search Report and Written Opinion dated Nov. 13, 2020.
PCT/US2020/052536 filed Sep. 24, 2020 International Search Report and Written Opinion dated Dec. 4, 2020.
PCT/US2020/056364 filed Oct. 19, 2020 International Search Report and Written Opinion dated Jan. 19, 2021.
PCT/US2020/056864 filed Oct. 22, 2020 International Search Report and Written Opinion dated Jan. 14, 2021.
PCT/US2020/057202 filed Oct. 23, 2020 International Search Report and Written Opinion dated Jan. 21, 2021.
PCT/US2020/057397 filed Oct. 26, 2020 International Search Report and Written Opinion dated Mar. 10, 2021.
U.S. Appl. No. 15/008,628, filed Jan. 28, 2016 Final Office Action dated May 30, 2018.
U.S. Appl. No. 15/008,628, filed Jan. 28, 2016 Non-Final Office Action dated Jan. 25, 2019.
U.S. Appl. No. 15/008,628, filed Jan. 28, 2016 Non-Final Office Action dated Nov. 2, 2017.
U.S. Appl. No. 15/008,628, filed Jan. 28, 2016 Notice of Allowance dated May 15, 2019.
U.S. Appl. No. 16/398,020, filed Apr. 29, 2019 Non-Final Office Action dated May 11, 2021.
PCT/US2021/028018 filed Apr. 19, 2021 International Preliminary Report on Patentability dated Jun. 3, 2022.
PCT/US2021/064671 filed Dec. 21, 2021 International Search Report and Written Opinion dated May 27, 2022.
PCT/US2022/024085 filed Apr. 8, 2022 International Search Report and Wirtten Opinion dated Sep. 12, 2022.
U.S. Appl. No. 16/398,020, filed Apr. 29, 2019 Examiner's Answer dated Oct. 31, 2022.
U.S. Appl. No. 17/031,478, filed Sep. 24, 2020 Notice of Allowance dated Sep. 16, 2022.
U.S. Appl. No. 17/156,252, filed Jan. 22, 2021 Non-Final Office Action dated Oct. 25, 2022.
PCT/US2021/044223 filed Aug. 2, 2021 International Search Report and Written Opinion dated Dec. 21, 2021.
PCT/US2021/048275 filed Aug. 30, 2021 International Search Report and Written Opinion dated Jan. 4, 2022.
PCT/US2021/064174 filed Dec. 17, 2021 International Search Report and Written Opinion dated May 18, 2022.
PCT/US2021/064642 filed Dec. 21, 2021 International Search Report and Written Opinion dated May 11, 2022.
U.S. Appl. No. 17/031,478, filed Sep. 24, 2020 Non-Final Office Action dated May 11, 2022.
PCT/US2021/039084 filed Jun. 25, 2021 International Search Report and Written Opinion dated Jan. 10, 2022.
U.S. Appl. No. 16/398,020, filed Apr. 29, 2019 Final Office Action dated Jan. 25, 2022.
U.S. Appl. No. 17/006,553, filed Aug. 28, 2020 Non-Final Office Action dated Mar. 16, 2022.
U.S. Appl. No. 17/077,728, filed Oct. 22, 2020 Non-Final Office Action dated Feb. 9, 2022.
PCT/US2022/039614 filed Aug. 5, 2022 International Search Report and Written Opinion dated Dec. 22, 2022.
PCT/US2022/044848 filed Sep. 27, 2022 International Search Report and Written Opinion dated Feb. 3, 2023.
PCT/US2022/044879 filed Sep. 27, 2022 International Search Report and Written Opinion dated Mar. 3, 2023.
PCT/US2022/044901 filed Sep. 27, 2022 International Search Report and Written Opinion dated Mar. 3, 2023.
PCT/US2022/044918 filed Sep. 27, 2022 International Search Report and Written Opinion dated Feb. 21, 2023.
PCT/US2022/044923 filed Sep. 27, 2022 International Search Report and Written Opinion dated Feb. 15, 2023.
U.S. Appl. No. 17/156,252, filed Jan. 22, 2021 Notice of Allowance dated Apr. 24, 2023.
U.S. Appl. No. 17/237,909, filed Apr. 22, 2021 Restriction Requirement dated Feb. 1, 2023.
U.S. Appl. No. 17/390,682, filed Jul. 30, 2021 Non-Final Office Action dated Mar. 2, 2023.
U.S. Appl. No. 17/392,061, filed Aug. 2, 2021 Restriction Requirement dated Mar. 30, 2023.
U.S. Appl. No. 17/156,252, filed Jan. 22, 2021 Notice of Allowance dated Aug. 9, 2023.
U.S. Appl. No. 17/237,909, filed Apr. 22, 2021 Non-Final Office Action dated Jul. 27, 2023.
U.S. Appl. No. 17/360,694, filed Jun. 28, 2021 Restriction Requirement dated Jul. 20, 2023.
U.S. Appl. No. 17/390,682, filed Jul. 30, 2021 Final Office Action dated Jul. 27, 2023.
U.S. Appl. No. 17/392,061, filed Aug. 2, 2021 Non-Final Office Action dated Jul. 17, 2023.
PCT/US2021/057135 filed Oct. 28, 2021 International Preliminary Report on Patentability dated May 2, 2023.
PCT/US2023/011173 filed Jan. 19, 2023 International Search Report and Written Opinion dated May 22, 2023.
U.S. Appl. No. 17/240,591, filed Apr. 26, 2021 Non-Final Office Action dated Jun. 8, 2023.
U.S. Appl. No. 17/358,504, filed Jun. 25, 2021 Restriction Requirement dated Jun. 7, 2023.

* cited by examiner

RAPIDLY INSERTABLE CENTRAL CATHETERS INCLUDING CATHETER ASSEMBLIES AND METHODS THEREOF

PRIORITY

This application claims the benefit of priority to U.S. Provisional Application No. 63/028,445, filed May 21, 2020, which is incorporated by reference in its entirety into this application.

BACKGROUND

A central venous catheter ("CVC") is formed of a material having a relatively low durometer, which contributes to the CVC having a lack of column strength. Due to the lack of column strength, CVCs are commonly introduced into patients and advanced through their vasculatures by way of the Seldinger technique. The Seldinger technique utilizes a number of steps and medical devices (e.g., a needle, a scalpel, a guidewire, an introducer sheath, a dilator, a CVC, etc.). While the Seldinger technique is effective, the number of steps are time consuming, handling the number of medical devices is awkward, and both of the foregoing can lead to patient trauma. In addition, there is a relatively high potential for touch contamination due to the number of medical devices that need to be interchanged during the number of steps of the Seldinger technique. As such, there is a need to reduce the number of steps and medical devices involved in introducing a catheter such as a CVC into a patient and advancing the catheter through a vasculature thereof.

Disclosed herein are rapidly insertable central catheters ("RICCs") including catheter assemblies and methods thereof that address the foregoing.

SUMMARY

Disclosed herein is a RICC assembly. The RICC assembly includes, in some embodiments, a RICC and an introducer. The RICC includes a catheter tube, a catheter hub coupled to a proximal-end portion of the catheter tube, and one or more extension legs, wherein each extension leg of the one-or-more extension legs is coupled to the catheter hub by a distal-end portion thereof. The catheter tube includes a first section, a second section, and a side aperture through a side of the catheter tube in a distal-end portion thereof but proximal of the first section of the catheter tube. The first section of the catheter tube is formed of a first material having a first durometer. The second section of the catheter tube is formed of a second material having a second durometer less than the first durometer. The side aperture opens into an introducing lumen of the catheter tube that extends from at least the side aperture to a distal end of the RICC. The introducer includes a retractable-needle device, a syringe, and a coupling hub coupling the retractable-needle device and the syringe together proximal of the side aperture in at least a ready-to-deploy state of the RICC assembly. The retractable-needle device includes an introducer needle. The introducer needle has a shaft and a needle tip in a distal-end portion of the shaft. The needle tip extends beyond the distal end of the RICC when the RICC assembly is in at least the ready-to-deploy state of the RICC assembly.

In some embodiments, the shaft of the introducer needle extends through a longitudinal through hole of the coupling hub, through the side aperture of the catheter tube, and along the introducing lumen of the catheter tube in at least the ready-to-deploy state of the RICC assembly.

In some embodiments, the coupling hub includes a sealed blood-flashback chamber. A cutout of the shaft of the introducer needle is disposed in the blood-flashback chamber. The cutout is configured to release blood into the blood-flashback chamber upon the needle tip accessing a blood-vessel lumen of a patient.

In some embodiments, the coupling hub includes a side arm extending from a side of the coupling hub. The syringe is fluidly coupled to the blood-flashback chamber by a side-arm lumen of the side arm for aspirating blood upon accessing the blood-vessel lumen.

In some embodiments, the introducer further includes a clip having a syringe-clipping portion and needle device-clipping portion. The syringe-clipping portion of the clip is configured to clip the syringe by a barrel of the syringe. The needle device-clipping portion of the clip is configured to clip the retractable-needle device by a body of the retractable-needle device while allowing the retractable-needle device to slide in the needle device-clipping portion of the clip.

In some embodiments, the syringe includes a plunger disposed in the barrel of the syringe. The plunger includes a plunger extension configured to allow a clinician to withdraw the plunger from the barrel by proximally pushing a tab of the plunger extension while handling the RICC assembly around the coupling hub.

In some embodiments, the coupling hub includes a tab configured to allow a clinician to single handedly advance the RICC over the needle tip with a single finger of a hand while holding a distal-end portion of the retractable-needle device between a thumb and another finger or fingers of the hand.

In some embodiments, the retractable-needle device further includes an access guidewire and an access-guidewire actuator. The access guidewire is disposed in a needle lumen of the introducer needle. The access-guidewire actuator is configured to advance a distal-end portion of the access guidewire beyond the needle tip. The access-guidewire actuator is also configured to withdraw the distal-end portion of the access guidewire into the distal-end portion of the shaft of the introducer needle proximal of the needle tip.

In some embodiments, the access-guidewire actuator includes a slider slidably disposed in a longitudinal slot of a housing of the retractable-needle device. The slider includes an extension coupled to a proximal-end portion of the access guidewire within a cavity of the retractable-needle device enclosed by the housing.

In some embodiments, a proximal-end portion of the introducer needle is disposed in a carriage of the retractable-needle device. When actuated, an introducer-needle actuator of the retractable-needle device is configured to release a compressed compression spring around the carriage and thrust both the carriage and the introducer needle proximally into the cavity of the retractable-needle device.

In some embodiments, the carriage is configured to engage the slider of the access-guidewire actuator when the carriage is thrust proximally into the cavity of the retractable-needle device. The access guidewire is withdrawn into the cavity of the retractable-needle device by the distal-end portion thereof together with the introducer needle when the introducer-needle actuator is actuated.

In some embodiments, the RICC further includes a sterile barrier over the catheter tube between the catheter hub and the side aperture of the catheter tube. The sterile barrier is configured to split apart when a sterile-barrier tab of a proximal-end portion of the sterile barrier is pulled away from the catheter tube by the sterile-barrier tab.

In some embodiments, the RICC includes a set of three lumens including a distal lumen, a medial lumen, and a proximal lumen formed of fluidly connected portions of three catheter-tube lumens, three hub lumens, and three extension-leg lumens. The introducing lumen of the catheter tube is coincident with a distal-end portion of the distal lumen.

In some embodiments, the distal lumen has a distal-lumen aperture in the distal end of the RICC. The medial lumen has a medial-lumen aperture in the side of the catheter tube proximal of the distal-lumen aperture. The proximal lumen has a proximal-lumen aperture in the side of the catheter tube proximal of the medial-lumen aperture. The side aperture of the catheter tube is between the distal-lumen aperture and the medial-lumen aperture, between the medial-lumen aperture and the proximal-lumen aperture, or proximal of the proximal-lumen aperture.

Also disclosed herein is a method for inserting a RICC into a blood-vessel lumen of a patient. The method includes, in some embodiments, a RICC assembly-obtaining step, a needle tract-establishing step, a RICC-advancing step, and an introducer needle-withdrawing step. The RICC assembly-obtaining step includes obtaining a RICC assembly. The RICC assembly includes the RICC and an introducer. The introducer includes a retractable-needle device and a syringe coupled together by a coupling hub. The retractable-needle device includes an introducer needle having a shaft extending through a longitudinal through hole of the coupling hub, through a side aperture in a distal-end portion of a catheter tube of the RICC, along an introducing lumen of the catheter tube, and beyond a distal end of the RICC in at least a ready-to-deploy state of the RICC assembly. The needle tract-establishing step includes establishing a needle tract from an area of skin to the blood-vessel lumen of the patient with a needle tip of the introducer needle while holding a distal-end portion of the retractable-needle device. The RICC-advancing step includes advancing a distal-end portion of the catheter tube into the blood-vessel lumen over the needle tip. The introducer needle-withdrawing step includes withdrawing the shaft of the introducer needle from the introducing lumen by way of the side aperture of the catheter tube.

In some embodiments, the needle tract-establishing step includes ensuring blood flashes back into a sealed blood-flashback chamber of the coupling hub. A cutout of the shaft of the introducer needle is disposed in the blood-flashback chamber for releasing blood into the blood-flashback chamber upon accessing the blood-vessel lumen of the patient.

In some embodiments, the method further includes a blood aspirating-step. The blood aspirating-step includes aspirating blood with the syringe after the needle tract-establishing step but before the introducer needle-withdrawing step. The syringe is fluidly coupled to the blood-flashback chamber by a side-arm lumen of a side arm of the coupling hub for the blood aspirating-step. The blood aspirating-step confirms the needle tip is disposed in the blood-vessel lumen of the patient.

In some embodiments, the RICC-advancing step includes advancing the catheter tube into the blood-vessel lumen with a single finger of a hand while holding a distal-end portion of the retractable-needle device between a thumb and another finger or fingers of the hand. The coupling hub includes a tab configured for advancing the catheter tube into the blood-vessel lumen with the single finger.

In some embodiments, the method further an access guidewire-advancing step. The access guidewire-advancing step includes advancing a distal-end portion of an access guidewire disposed in a needle lumen of the introducer needle into the blood-vessel lumen. The distal-end portion of the access guidewire is advanced by sliding a slider slidably disposed in a longitudinal slot of a housing of the retractable-needle device. The slider includes an extension coupled to a proximal-end portion of the access guidewire disposed in a cavity of the retractable-needle device enclosed by the housing. The access guidewire-advancing step is performed before the RICC-advancing step.

In some embodiments, the introducer needle-withdrawing step includes actuating an introducer-needle actuator of the retractable-needle device. A proximal-end portion of the introducer needle is disposed in a carriage of the retractable-needle device configured to thrust proximally into the cavity of the retractable-needle device when a compressed compression spring around the carriage is released by the introducer-needle actuator.

In some embodiments, the method further a maneuver guidewire-advancing step. The maneuver guidewire-advancing step includes advancing a maneuver guidewire into the blood-vessel lumen by way of a distal lumen having a distal-lumen aperture in the distal end of the RICC. The introducing lumen of the catheter tube is coincident with a distal-end portion of the distal lumen, which mandates performing the introducer needle-withdrawing step before the maneuver guidewire-advancing step.

In some embodiments, the method further includes a sterile barrier-removing step. The sterile barrier-removing step includes removing a sterile barrier disposed over the catheter tube between a catheter hub of the RICC and the side aperture of the catheter tube. The sterile barrier is removed by pulling a sterile-barrier tab of a proximal-end portion of the sterile barrier away from the catheter tube to split the sterile barrier apart.

In some embodiments, the catheter tube includes a first section formed of a first material having a first durometer and a second section proximal of the first section formed of a second material having a second durometer less than the first durometer. The first section of the catheter tube is configured with a column strength for advancing the catheter tube into the blood-vessel lumen.

These and other features of the concepts provided herein will become more apparent to those of skill in the art in view of the accompanying drawings and following description, which describe particular embodiments of such concepts in greater detail.

DRAWINGS

DESCRIPTION

Figure 1:
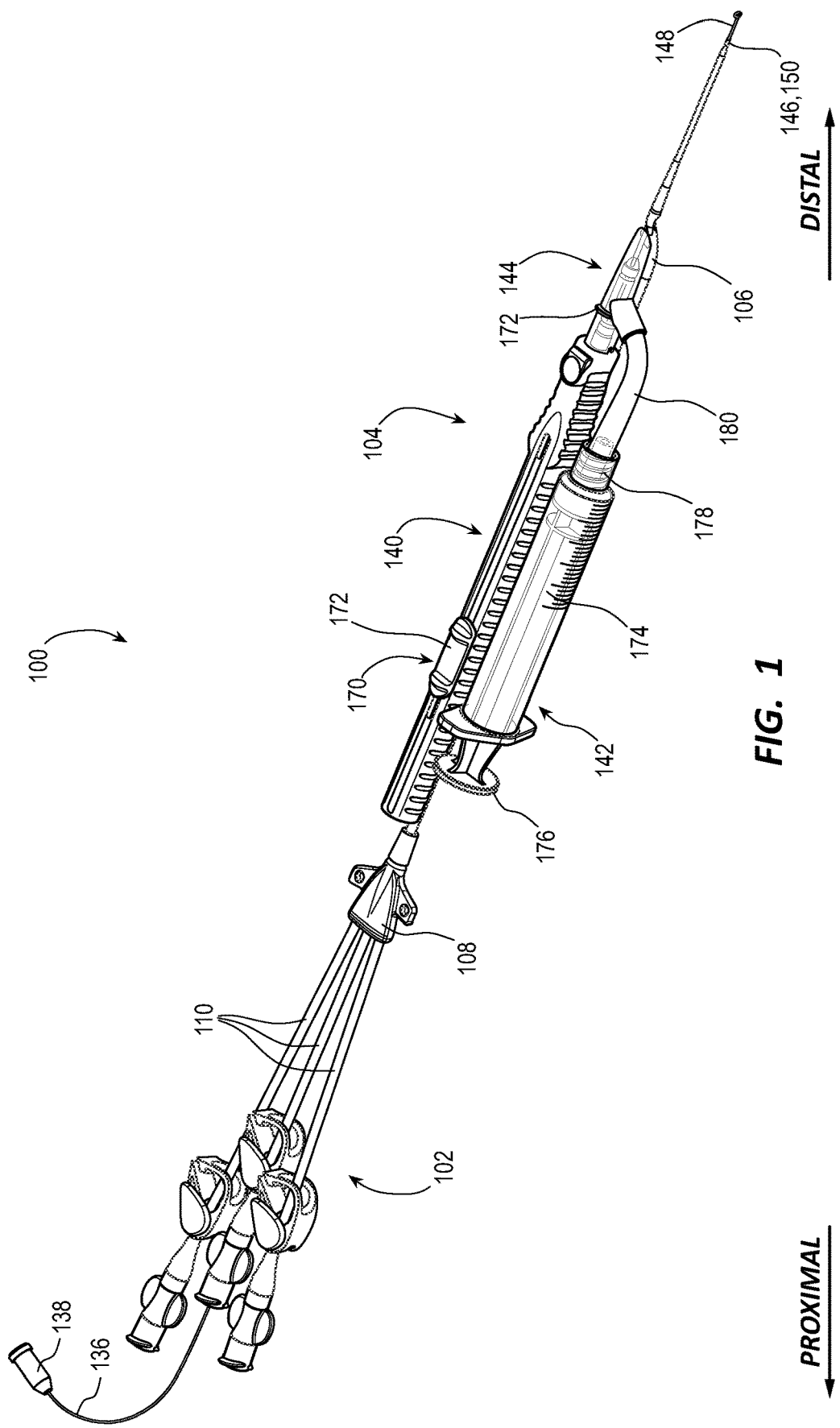
FIG. 1 illustrates an oblique view of a RICC assembly including a RICC and an introducer in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

As set forth above, there is a need to reduce the number of steps and medical devices involved in introducing a catheter such as a CVC into a patient and advancing the catheter through a vasculature thereof.

Disclosed herein are RICCs including catheter assemblies and methods thereof that address the foregoing. However, it should be understood the RICCs are but one type of catheter in which the concepts provided herein can be embodied or otherwise incorporated. Indeed, peripherally inserted central catheters ("PICCs"), dialysis catheters, or the like can also embody or otherwise incorporate the concepts provided herein for the RICCs, as well as catheter assemblies and methods thereof.

RICC Assemblies

Figure 2:
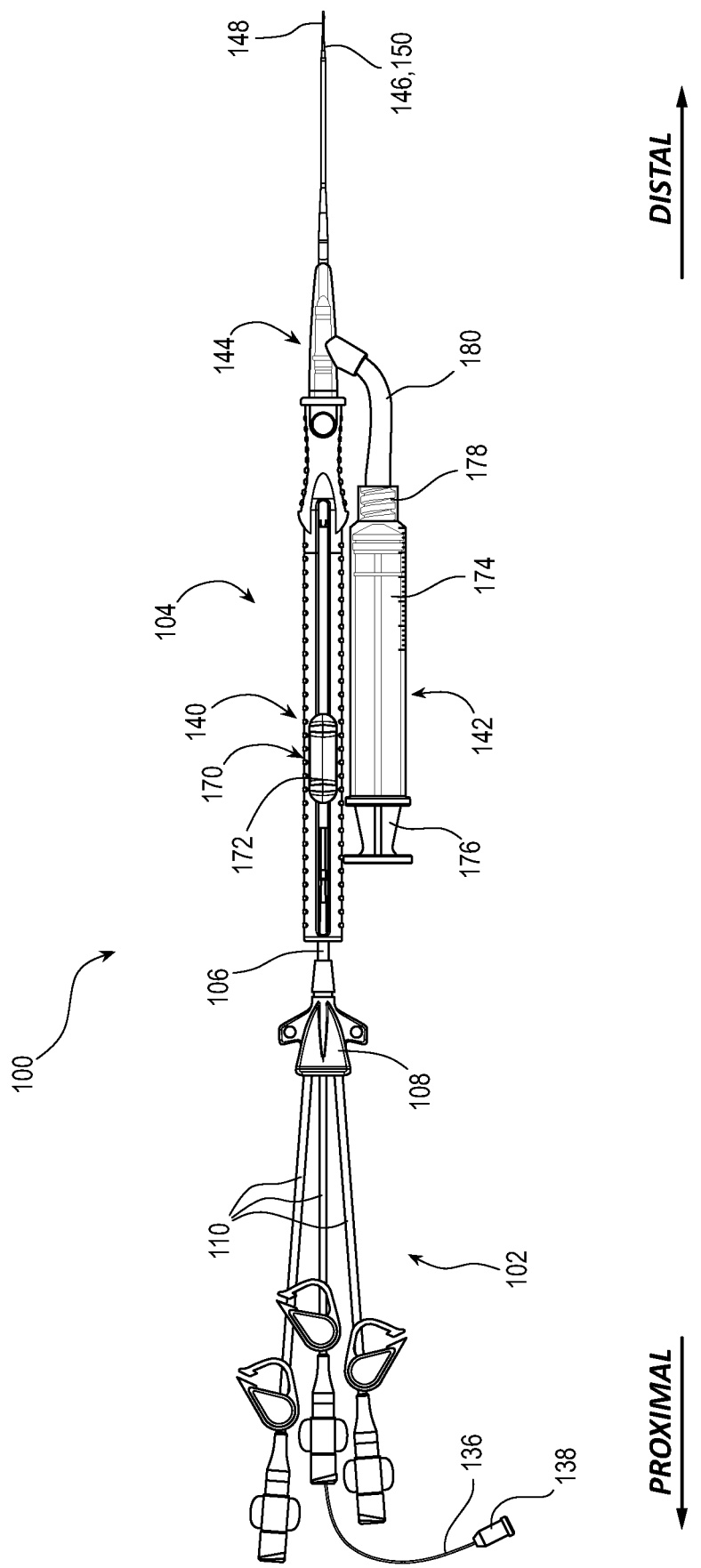
FIG. 2 illustrates a top view of the RICC assembly in accordance with some embodiments.
Figure 3:
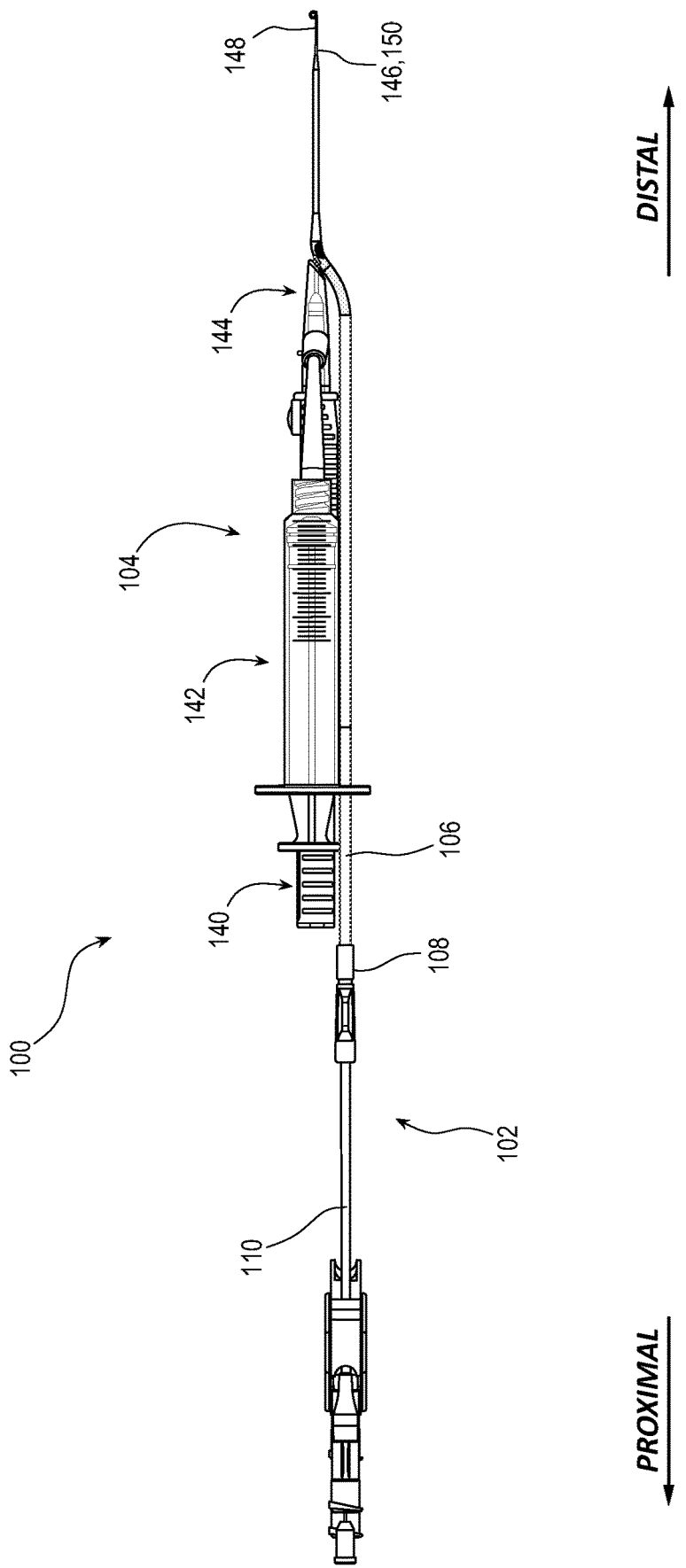
FIG. 3 illustrates a side view of the RICC assembly in accordance with some embodiments.
Figure 4:
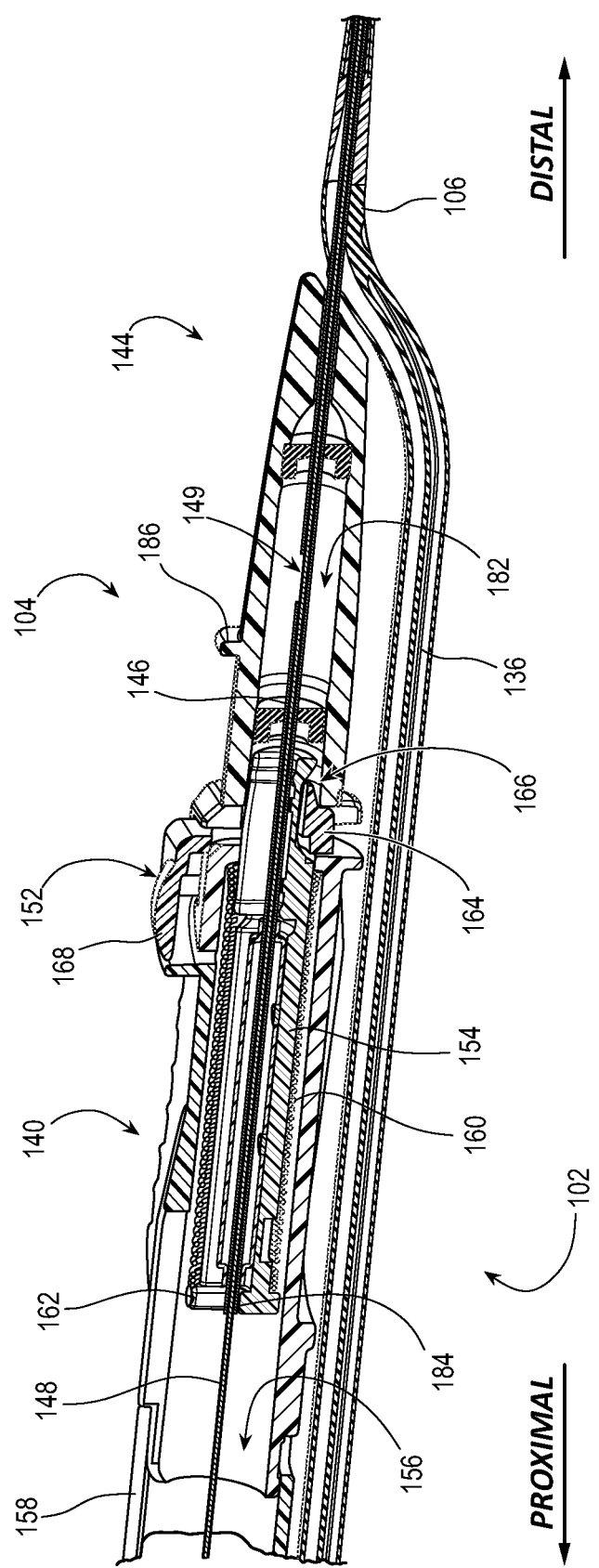
FIG. 4 illustrates a longitudinal cross section of the RICC assembly in accordance with some embodiments.
Figure 5:
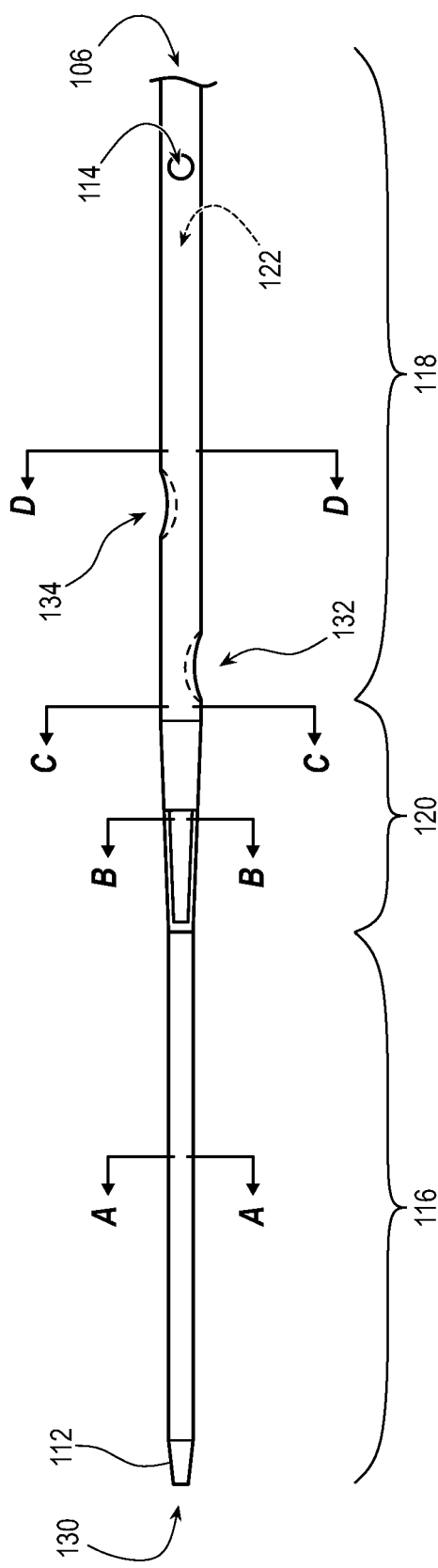
FIG. 5 illustrates a distal-end portion of a catheter tube of the RICC in accordance with some embodiments.
Figure 8:
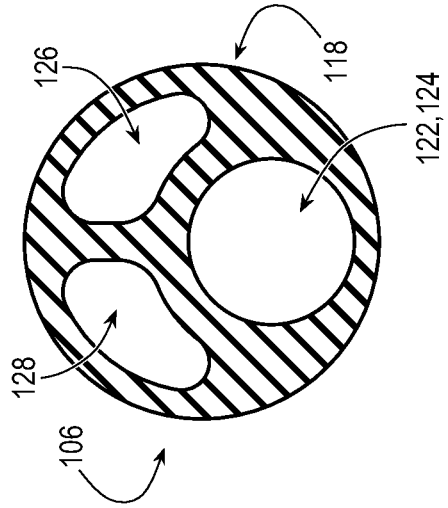
FIG. 8 illustrates a third or fourth transverse cross section of the catheter tube in accordance with some embodiments.
Figure 7:
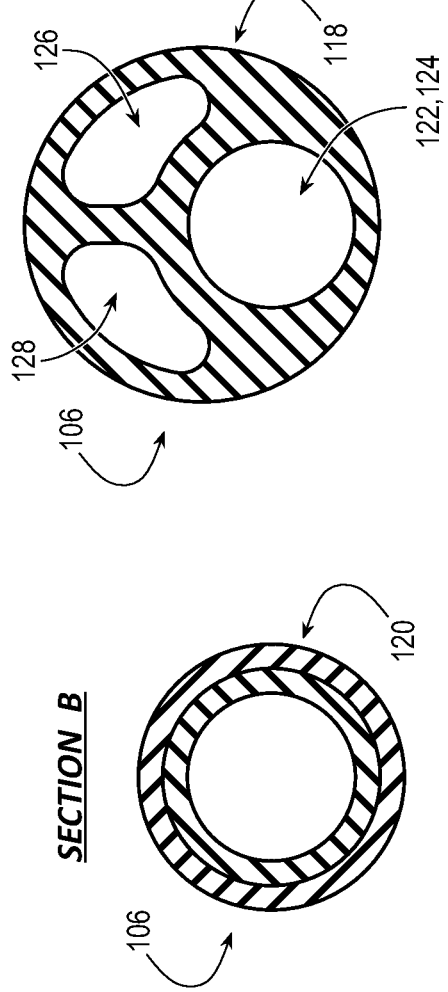
FIG. 7 illustrates a second transverse cross section of the catheter tube in accordance with some embodiments.
Figure 6:
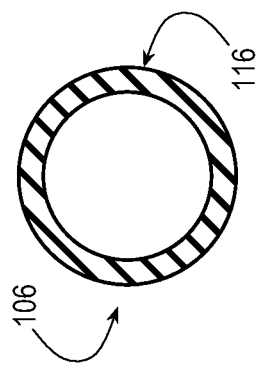
FIG. 6 illustrates a first transverse cross section of the catheter tube in accordance with some embodiments.
Figure 9:
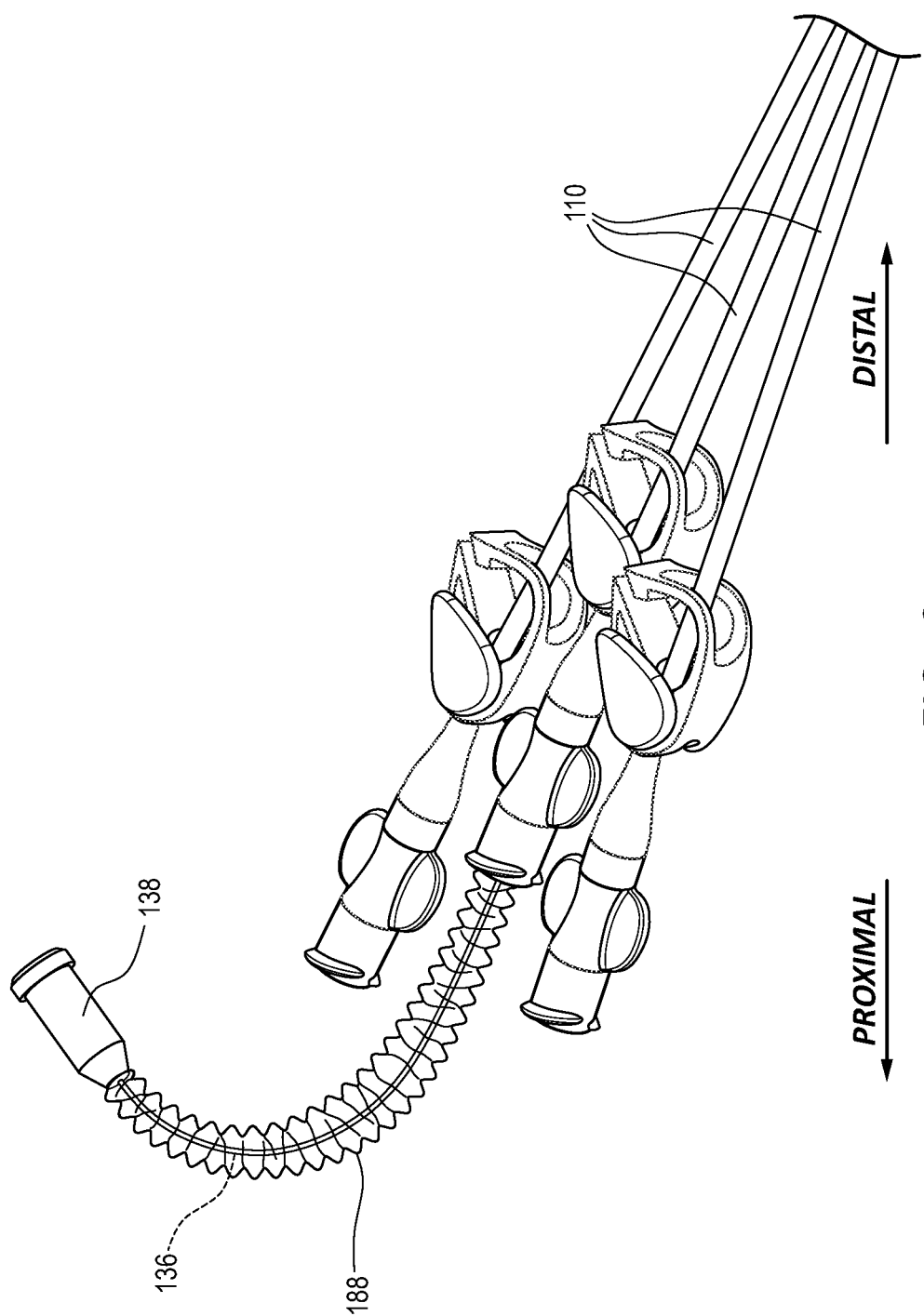
FIG. 9 illustrates a sterile barrier over a maneuver guidewire of the RICC assembly in accordance with some embodiments.
Figure 10:
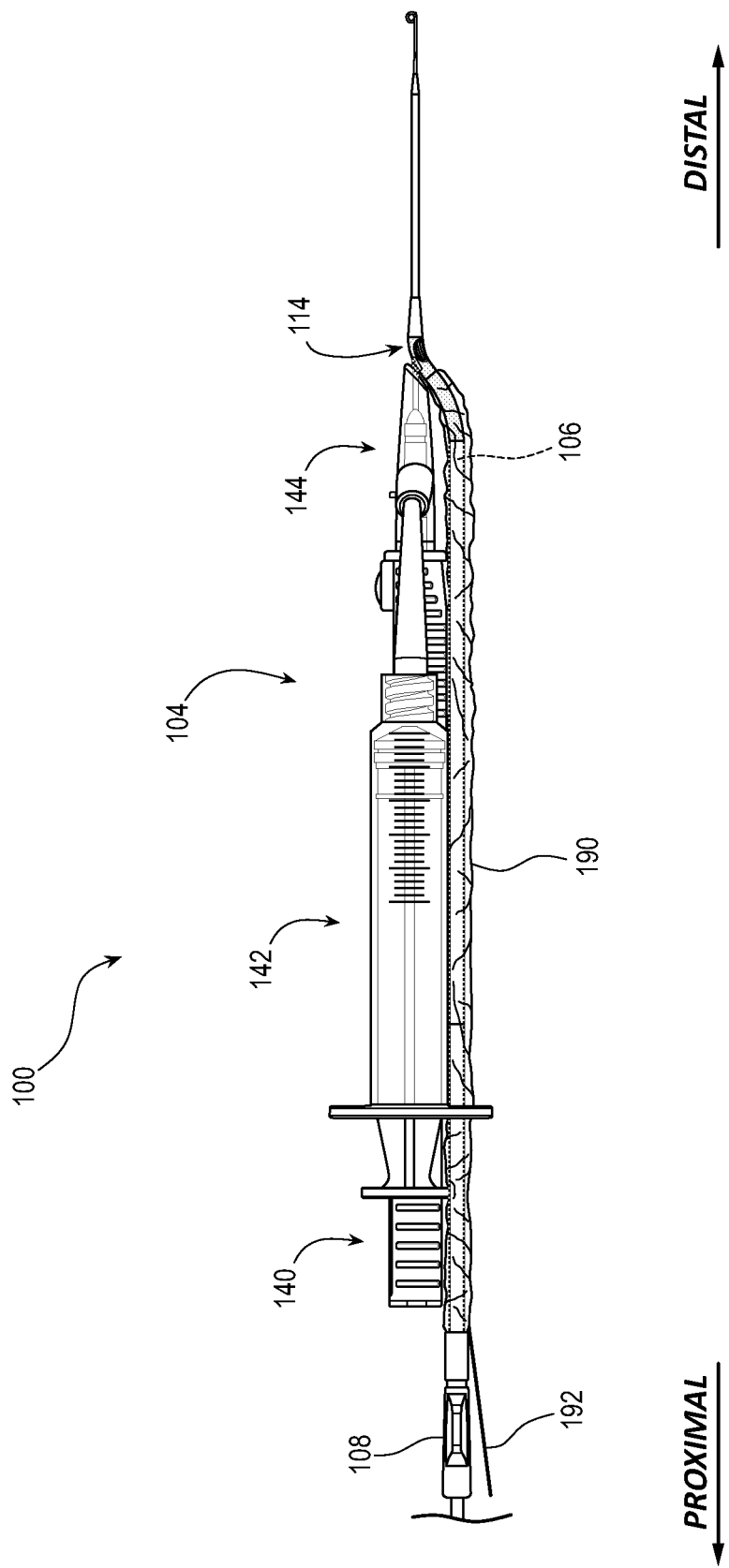
FIG. 10 illustrates a sterile barrier over the catheter tube in accordance with some embodiments.
Figure 11:
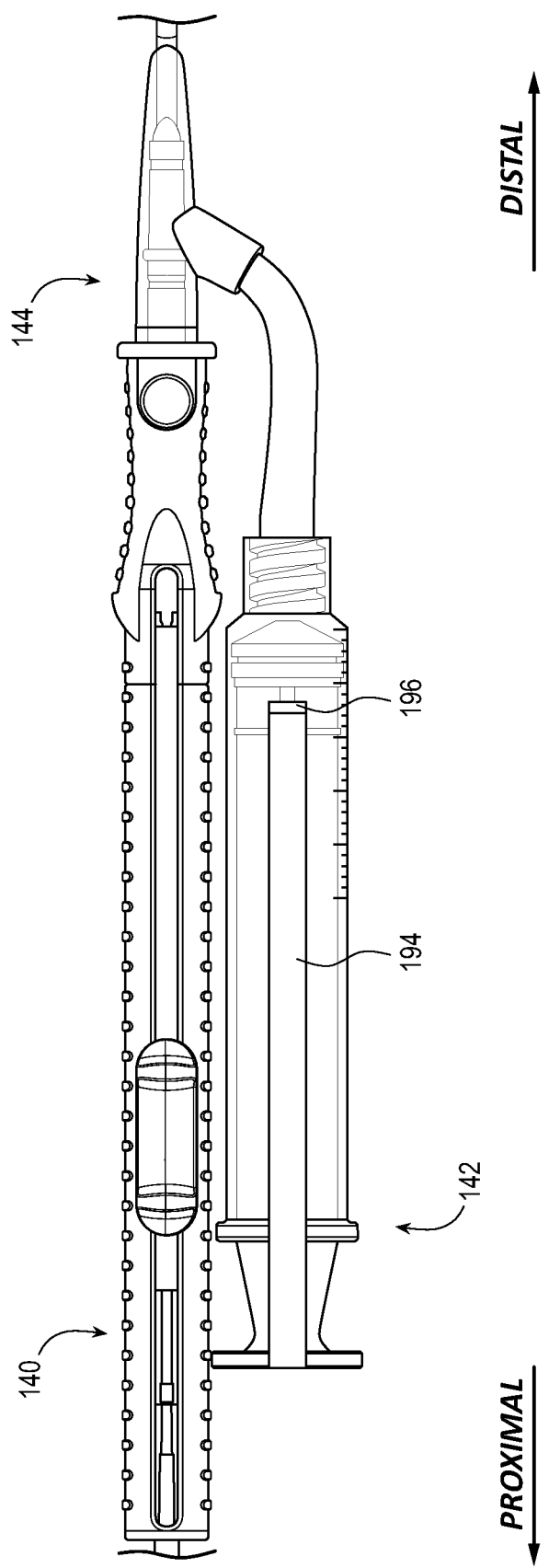
FIG. 11 illustrates a plunger extension of a syringe of the introducer in accordance with some embodiments.
Figure 12:
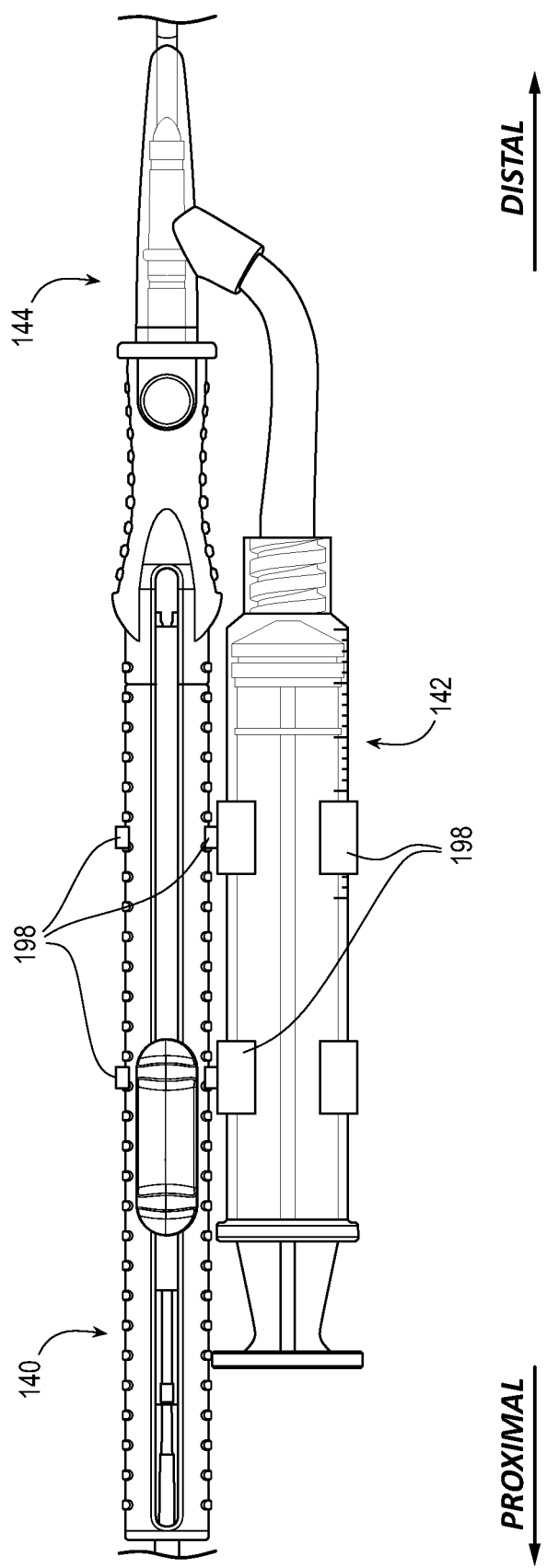
FIG. 12 illustrates a clip of the introducer in accordance with some embodiments.

FIGS. 1-3 illustrate various views of a RICC assembly 100 including a RICC 102 and an introducer 104 in accordance with some embodiments. FIG. 4 illustrates a longitudinal cross section of the RICC assembly 100 in accordance with some embodiments. FIG. 5 illustrates a distal-end portion of a catheter tube 106 of the RICC 102 in accordance with some embodiments. FIGS. 6-8 illustrate various transverse cross-sections of the catheter tube 106 in accordance with some embodiments. FIGS. 9-12 illustrate various other features of the RICC assembly 100 in accordance with some embodiments.

As shown, the RICC assembly 100 includes, in some embodiments, the RICC 102 and the introducer 104. The RICC 102 and the introducer 104 are described, in turn, in sections set forth below; however, some crossover between the sections for the RICC 102 and the introducer 104 exist in view of the interrelatedness of the RICC 102 and the introducer 104 in the RICC assembly 100.

The RICC 102 includes the catheter tube 106, a catheter hub 108, and one or more extension legs 110.

The catheter tube 106 includes two or more sections including a catheter tip 112 in a distal-end portion of the catheter tube 106, one or more catheter-tube lumens, and a side aperture 114 through a side of the catheter tube 106 in the distal-end portion of the catheter tube 106.

The two or more sections of the catheter tube 106 can be a main body of the catheter tube 106 and the catheter tip 112, which can be formed as a single extruded piece of a single material or a single coextruded piece of two similar materials. Alternatively, the main body of the catheter tube 106 and the catheter tip 112 can be formed as two different extruded pieces of two similar materials and subsequently coupled. However, FIG. 5 illustrates an embodiment of the catheter tube 106 in which the catheter tube 106 is formed as two different extruded pieces of two different materials and subsequently coupled. Indeed, the catheter tube 106 includes a first section 116 including the catheter tip 112, a second section 118 including the side aperture 114, and an optional transition section 120 therebetween depending upon the manner in which the first section 116 and the second section 118 of the catheter tube 106 are coupled. For example, the first and second sections 116 and 118 of the catheter tube 106 can be bonded by heat, solvent, or adhesive such that the first and second sections 116 and 118 abut each other, or the second section 118 can be inserted into the first section 116 and bonded thereto by heat, solvent, or adhesive, thereby forming the transition section 120. Advantageously, the latter coupling of inserting the second section 118 into the first section 116 facilitates incorporation of a smooth taper into the transition section 120, which taper is useful for dilation during methods of using the RICC assembly 100.

The first section 116 of the catheter tube 106 can be formed of a first material (e.g., a polymeric material such as polytetrafluoroethylene, polypropylene, or polyurethane) having a first durometer, while the second section 118 of the catheter tube 106 can be formed of a second material (e.g., a polymeric material such as polyvinyl chloride, polyethylene, polyurethane, or silicone) having a second durometer less than the first durometer. For example, each section of the first section 116 and the second section 118 of the catheter tube 106 can be made from a different polyurethane having a different durometer. Indeed, polyurethane is advantageous in that polyurethane sections of the catheter tube 106 can be relatively rigid at room-temperature but become more flexible in vivo at body temperature, which reduces irritation to vessel walls and phlebitis. Polyurethane is also advantageous in that can be less thrombogenic than some other polymers.

The catheter tube 106 having at least the first section 116 of the first polymeric material and the second section 118 of the second polymeric material has a column strength sufficient to prevent buckling of the catheter tube 106 when the catheter tube 106 is inserted into an insertion site and advanced through a vasculature of a patient. The column strength of the catheter tube 106 is notable in that it makes it possible to rapidly insert the catheter tube 106 into the insertion site and advance the catheter tube 106 through the vasculature of the patient without using the Seldinger technique.

It should be understood the first durometer and the second durometer can be on different scales (e.g., Type A or Type D), so the second durometer of the second polymeric material might not be numerically less than the first durometer of the first polymeric material. That said, the hardness of the second polymeric material can still be less than the hardness of the first polymeric material as the different scales—each of which ranges from 0 to 100—are designed for characterizing different materials in groups of the materials having a like hardness.

Notwithstanding the foregoing, the first section 116 and the second section 118 of the catheter tube 106 can be formed of a same polymeric material or different polymeric materials having substantially equal durometers provided a column strength of the catheter tube 106 is sufficient to prevent buckling of the catheter tube 106 when inserted into a needle tract to a blood-vessel lumen and advanced through a vasculature of a patient.

The one-or-more catheter-tube lumens can extend through an entirety of the catheter tube 106; however, only one catheter-tube lumen typically extends from a proximal end of the catheter tube 106 to a distal end of the catheter tube 106 in a multiluminal RICC (e.g., a diluminal RICC, a triluminal RICC, a tetraluminal RICC, a pentaluminal RICC, a hexaluminal RICC, etc.). Indeed, the catheter tip 112 typically includes a single lumen therethrough. Optionally, the single lumen through the catheter tip 112 can be referred to as a "tip lumen," particularly in reference to the first section 116 of the catheter tube 106, which is formed separately from a remainder of the catheter tube 106 and coupled thereto.

Again, the side aperture 114 is through a side of the catheter tube 106 in the distal-end portion of the catheter tube 106; however, the side aperture 114 is proximal of the first section 116 of the catheter tube 106. The side aperture 114 opens into an introducing lumen 122 of the one-or-more catheter-tube lumens. The introducing lumen 122 extends from at least the side aperture 114 in the second section 118 of the catheter tube 106, through the first section 116 of the catheter tube 106 distal thereof, and to a distal end of the RICC 102 (e.g., the distal end of the catheter tube 106 or a distal end of the catheter tip 112). The introducing lumen 122 is coincident with a distal-end portion of the one catheter-tube lumen set forth above that typically extends from the proximal end of the catheter tube 106 to the distal end of the catheter tube 106, particularly the distal-end portion of the foregoing catheter-tube lumen distal of the side aperture 114.

The catheter hub 108 is coupled to a proximal-end portion of the catheter tube 106. The catheter hub 108 includes one or more catheter-hub lumens corresponding in number to the one-or-more catheter-tube lumens. The one-or-more catheter-hub lumens extend through an entirety of the catheter hub 108 from a proximal end of the catheter hub 108 to a distal end of the catheter hub 108.

Each extension leg of the one-or-more extension legs 110 is coupled to the catheter hub 108 by a distal-end portion thereof. The one-or-more extension legs 110 respectively include one or more extension-leg lumens, which, in turn, correspond in number to the one-or-more catheter-tube lumens. Each extension-leg lumen of the one-or-more extension-leg lumens extends through an entirety of the extension leg from a proximal end of the extension leg to a distal end of the extension leg.

Each extension leg of the one-or-more extension legs 110 typically includes a Luer connector coupled to the extension leg, through which Luer connector the extension leg and the extension-leg lumen thereof can be connected to another medical device.

While the RICC 102 can be a monoluminal or multiluminal RICC (e.g., a diluminal RICC, a triluminal RICC, a tetraluminal RICC, a pentaluminal RICC, a hexaluminal RICC, etc.), the RICC 102 shown in FIGS. 1-8 is triluminal including a set of three lumens. The set of three lumens includes, for example, a distal lumen 124, a medial lumen 126, and a proximal lumen 128 formed of fluidly connected portions of three catheter-tube lumens, three hub lumens, and three extension-leg lumens. Whether the RICC 102 is monoluminal or multiluminal, the RICC 102 includes at least the distal lumen 124. The distal lumen 124 includes at least the one catheter-tube lumen set forth above that typically extends from the proximal end of the catheter tube 106 to the distal end of the catheter tube 106 as a catheter tube-lumen portion of the distal lumen 124, as well as a fluidly connected hub- and extension leg-lumen portions of the distal lumen 124. In accordance with the foregoing catheter-tube lumen, the introducing lumen 122 of the catheter tube 106 is coincident with a distal-end portion of the distal lumen 124, particularly the distal-end portion of the distal lumen 124 distal of the side aperture 114.

Further with respect to the triluminal embodiment of the RICC 102, the distal lumen 124 has a distal-lumen aperture 130 in the distal end of the RICC 102 (e.g., the distal end of the catheter tube 106 or the distal end of the catheter tip 112). The medial lumen 126 has a medial-lumen aperture 132 in the side of the catheter tube 106 proximal of the distal-lumen aperture 130 and distal of the following proximal-lumen aperture such that the medial lumen 126 is between the distal-lumen aperture 130 and the proximal-lumen aperture. The proximal lumen 128 has a proximal-lumen aperture 134 in the side of the catheter tube 106 proximal of the medial-lumen aperture 132. The side aperture 114 of the catheter tube 106 can be between the distal-lumen aperture 130 and the medial-lumen aperture 132, between the medial-lumen aperture 132 and the proximal-lumen aperture 134, or proximal of the proximal-lumen aperture 134 as shown in FIG. 5 such that each lumen aperture of the distal-lumen aperture 130, the medial-lumen aperture 132, and the proximal-lumen aperture 134 is distal of the side aperture 114.

The RICC 102 can further include a maneuver guidewire 136. While not shown, the maneuver guidewire 136 can include an atraumatic tip (e.g., a coiled or partially coiled tip) and a length sufficient for advancing the maneuver guidewire 136 to the lower ⅓ of the superior vena cava ("SVC") of the heart. The maneuver guidewire 136 can be captively disposed in the RICC 102 in at least a ready-to-deploy state of the RICC assembly 100. For example, the maneuver guidewire 136 can be disposed in the distal lumen 124 of the RICC 102 with a proximal-end portion or a medial portion of the maneuver guidewire 136 disposed in the extension leg-lumen portion of the distal lumen 124, the medial portion or a distal-end portion of the maneuver guidewire 136 disposed in the hub-lumen portion of the distal lumen 124, and the distal-end portion of the maneuver guidewire 136 disposed in the catheter tube-lumen portion of the distal lumen 124, which is formed of the one catheter-tube lumen set forth above that typically extends from the proximal end of the catheter tube 106 to the distal end of the catheter tube 106. However, the distal-end portion of the foregoing catheter-tube lumen distal of the side aperture 114 is coincident with the introducing lumen 122, which, as set forth below, is occupied by the introducer needle 146 in at least the ready-to-deploy state of the RICC assembly 100. Due to the presence of the introducer needle 146 in the introducing lumen 122, a distal end of the maneuver guidewire 136 is just short of the side aperture 114 in at least the ready-to-deploy state of the RICC assembly 100.

The maneuver guidewire 136 can include a stop 138 (e.g., a hub, a ball, a slug, etc.) about a proximal-end portion of the maneuver guidewire 136 forming a stop end (e.g., a hub end, a ball end, a slug end, etc.) of the maneuver guidewire 136. The stop end of the maneuver guidewire 136 is larger than a proximal-end opening of the distal lumen 124 or the extension leg-lumen portion thereof, thereby providing a distal limit for advancing the maneuver guidewire 136 into the RICC 102. In addition, the maneuver guidewire 136 can be disposed in a fixed-length sterile barrier 188 (e.g., a longitudinal bag) including a closed or sealed proximal end and an otherwise open distal end removably coupled (e.g., removably adhered) to a proximal end of the Luer connector of the extension leg for manual removal of both the sterile barrier and the maneuver guidewire 136 when needed. A combination of the fixed length of the sterile barrier, the closed or sealed proximal end of the sterile barrier, and the distal end of the sterile barrier coupled to the Luer connector provides a limited tract within which the maneuver guidewire 136 can proximally move, thereby providing a proximal limit for withdrawing the maneuver guidewire 136 from the RICC 102. The proximal limit keeps the atraumatic tip of the maneuver guidewire 136 in the distal lumen 124 where, in at least the embodiment of the atraumatic tip having the coiled or partially coiled tip, the atraumatic tip remains in a straightened or uncoiled state, as discussed, for example, in U.S. Pat. Pub. No. 2015/0038943 and U.S. Pat. Pub. No. 2016/0015943, each of which is incorporated by reference in its entirety into this application. This is advantageous for it can be particularly difficult to reinsert such a guidewire in a lumen of a medical device such as a catheter.

Optionally, the stop end of the maneuver guidewire 136 is coupled (e.g., adhered) to the proximal end of the sterile barrier to maintain the stop end of the maneuver guidewire 136 in the proximal end of the sterile barrier, thereby reducing a mismatch between a length of the proximal-end portion of the maneuver guidewire 136 extending beyond the proximal end of the RICC 102 (e.g., a proximal end of the Luer connector) and an unpleated length of the sterile barrier. Reducing the mismatch between the foregoing lengths reduces a likelihood of losing the stop end of the maneuver guidewire 136 in a medial portion of the sterile barrier, which could require time and effort to rematch that would be better spent focusing on the patient.

In addition to providing the proximal limit for withdrawing the maneuver guidewire from the RICC 102, the sterile barrier is configured to maintain sterility of the maneuver guidewire 136 both before use (e.g., shipping and handling, storage, etc.) of the RICC assembly 100 and during use of the RICC assembly 100. During use of the RICC assembly 100, the sterile barrier is configured to provide a no-touch advancing means for advancing the maneuver guidewire 136 into a blood-vessel lumen of a patient upon establishing a needle tract thereto. Likewise, the sterile barrier is configured to provide a no-touch withdrawing means for withdrawing the maneuver guidewire 136 from the blood-vessel lumen of the patient, for example, after the catheter tube 106 has been advanced over the maneuver guidewire 136.

While not shown, the RICC 102 can further include stiffening stylets such as a stylet in either lumen or both lumens of the medial lumen 126 and the proximal lumen 128 of the triluminal embodiment of the RICC 102 for stiffening the RICC 102, thereby providing additional column strength to prevent buckling of the catheter tube 106 when the catheter tube 106 is inserted into an insertion site and advanced through a vasculature of a patient.

The RICC 102 can further include a sterile barrier 190 (e.g., a bag, a casing, etc.) configured to maintain sterility of the catheter tube 106 between the catheter hub 108 and the side aperture 114 of the catheter tube 106 prior to insertion of the catheter tube 106 into a blood-vessel lumen of a patient. When present, the sterile barrier 190 is over the catheter tube 106 between the catheter hub 108 and the side aperture 114 of the catheter tube 106 in at least the ready-to-deploy state of the RICC assembly 100. The sterile barrier 190 is configured to split apart when a sterile-barrier tab 192 of a proximal-end portion of the sterile barrier 190 is pulled away from the catheter tube 106, thereby providing a no-touch mechanism for removing the sterile barrier 190 from the catheter tube 106.

The introducer 104 includes a safety-needle device such as a retractable-needle device 140, a syringe 142, and a coupling hub 144 configured to couple the retractable-needle device 140 and the syringe 142 together. Excepting, for example, a distal-end portion of the introducer needle 146 set forth below, the introducer 104 is proximal of the side aperture 114 of the catheter tube 106 in at least the ready-to-deploy state of the RICC assembly 100 as shown in FIG. 4.

The safety-needle device is configured for ensuring safety of a clinician from injury (e.g., inadvertent needle sticks), contamination, or both while using the RICC assembly 100.

For example, the retractable-needle device 140 includes an introducer needle 146, an introducer-needle actuating mechanism configured to retract the introducer needle 146, an access guidewire 148, and an access-guidewire actuating mechanism configured to advance or withdraw the access guidewire 148. One example of an introducer-needle actuating mechanism that retracts the introducer needle 146 to prevent injury, and an access-guidewire actuating mechanism withdraws the access guidewire 148 to prevent contamination is the AccuCath Ace™ Intravascular Catheter System (Becton, Dickinson and Company (BD), Franklin Lakes, N.J.), aspects of which are disclosed in U.S. Pat. Nos. 8,728,035, 9,162,037, and 10,220,191, each of which is incorporated by reference in its entirety into this application. The safety-needle device can alternatively be based upon design principles of the PowerGlide® Midline Catheter products such as the PowerGlide PRO™ Midline Catheter (BD, Franklin Lakes, N.J.), aspects of which are disclosed in U.S. Pat. Nos. 8,721,546, 8,932,258, 8,986,227, 8,998,852, 9,757,540, 9,872,971, 9,950,139, 10,086,171, 10,384,039, and U.S. Pat. No. 10,426,931, each of which is incorporated by reference in its entirety into this application.

The introducer needle 146 has a shaft, a needle lumen along a length of the shaft, a cutout 149 in a side of the shaft that opens into the needle lumen, and a needle tip 150 (e.g., a beveled tip) in a distal-end portion of the shaft. In at least the ready-to-deploy state of the RICC assembly 100, a proximal-end portion of the shaft including the cutout 149 is disposed in the blood-flashback chamber 182 of the coupling hub 144 set forth below, whereas the distal-end portion of the shaft extends through the longitudinal through hole of the coupling hub 144 set forth below, through the side aperture 114 of the catheter tube 106, and along the introducing lumen 122 of the catheter tube 106 in the ready-to-deploy state of the RICC assembly 100. The needle tip 150 extends beyond the distal end of the RICC 102 when the RICC assembly 100 is in at least the ready-to-deploy state of the RICC assembly 100.

The introducer-needle actuating mechanism includes an introducer-needle actuator 152 and a carriage 154 disposed in a cavity 156 enclosed or otherwise defined by a body-forming housing 158 of the retractable-needle device 140. A proximal-end portion of the introducer needle 146 (e.g., the proximal-end portion of the shaft) is disposed in the carriage 154 as well. The carriage 154 can be spring loaded with a compressed compression spring 160 around the carriage 154, wherein the compression spring 160 is compressed between a proximal flange 162 of the carriage 154 and a distal-end piece of the retractable-needle device 140 (e.g., a distal wall of the housing 158) in at least the ready-to-deploy state of the RICC assembly 100. The introducer-needle actuator 152 can include a catch 164 configured to hold the spring-loaded carriage 154 by a complementary recess 166 in a coupling hub-connecting portion of the carriage 154 extending through a distal end of the retractable-needle device 140 or the housing 158 thereof. When the foregoing introducer-needle actuator 152 is toggled, for example, by a button 168 of the introducer-needle actuator 152, the introducer-needle actuator 152 dislodges the catch 164 from the recess 166 in the coupling hub-connecting portion of the carriage 154, thereby releasing the spring-loaded carriage 154 and the compression spring 160 therearound. Releasing the spring-loaded carriage 154 allows the compressed compression spring 160 to relax, which allows potential energy stored by the compressed compression spring 160 to be released. When relaxing, the compression spring 160 proximally extends and thrusts both the carriage 154 and the introducer needle 146 into the cavity 156 of the retractable-needle device 140.

The access guidewire 148 is captively disposed in a combination of the cavity 156 of the retractable-needle device 140 and the needle lumen of the introducer needle 146. In at least the ready-to-deploy state of the RICC assembly 100, a proximal-end portion of the access guidewire 148 is disposed in the cavity 156 and a distal-end portion of the access guidewire 148 is disposed in the needle lumen. Advantageously, a majority of the access guidewire 148 is contained within the retractable-needle device 140 during most if not all operating states of a number of operating states of the RICC assembly 100. Containing the access guidewire 148 within the retractable-needle device 140 also contains any blood or other bodily fluids within the retractable-needle device 140 that result from withdrawing the access guidewire 148 from a blood-vessel lumen of a patient. This minimizes or prevents a potential for contaminating an operating field or any clinicians operating within the operating field with the blood or other bodily fluids.

The access-guidewire actuating mechanism includes an access-guidewire actuator 170 coupled to the proximal-end portion of the access guidewire 148 disposed within the housing 158 of the retractable-needle device 140. For example, the access-guidewire actuator 170 includes a slider 172 slidably disposed in a closed-ended longitudinal slot of the housing 158 of the retractable-needle device 140, the closed ends of the longitudinal slot providing distal and proximal stops for advancing and withdrawing the access guidewire 148, respectively. While not shown, the slider 172 can include an extension extending into the cavity 156 of the retractable-needle device 140 where it is coupled to the proximal-end portion of the access guidewire 148. The foregoing access-guidewire actuator 170 is configured to advance the distal-end portion of the access guidewire 148 beyond the needle tip 150 when the access-guidewire actuator 170 is distally moved in accordance with the longitudinal slot. Likewise, the access-guidewire actuator 170 is configured to withdraw the access guidewire 148 into the retractable-needle device 140 such as the distal-end portion of the access guidewire 148 into the distal-end portion of the shaft or needle lumen proximal of the needle tip 150 when the access-guidewire actuator 170 is proximally moved in accordance with the longitudinal slot.

The access-guidewire actuator 170 can be actuated to withdraw the access guidewire 148 into the retractable-needle device 140 by manual actuation as set forth above or automatic actuation. With respect to automatic actuation, the carriage 154 of the introducer-needle actuating mechanism can be configured to engage the access-guidewire actuator 170 when the carriage 154 is thrust proximally into the cavity 156 of the retractable-needle device 140 by the compression spring 160 as the compression spring 160 relaxes. For example, a proximal end of the carriage 154 can be configured to engage a distal end of the slider 172 or the extension thereof when the carriage 154 is thrust proximally into the cavity 156 of the retractable-needle device 140 by the compression spring 160. The access guidewire 148 is withdrawn into the cavity 156 of the retractable-needle device 140 by the distal-end portion thereof together with the introducer needle 146 when the introducer-needle actuator 152 is automatically actuated.

The syringe 142 includes a barrel 174, a plunger 176 disposed in the barrel 174, and a syringe tip 178 extending from a distal end of the barrel 174, which is fluidly coupled to the side arm 180 of the coupling hub 144 set forth below at least when the RICC assembly 100 is in at least the ready-to-deploy thereof.

As shown, the plunger 176 can include a plunger extension 194 distally extending from a distal-end portion of the plunger along the barrel 174 of the syringe. The plunger extension 194 includes a tab 196 configured to allow a clinician to withdraw the plunger 176 from the barrel 174 of the syringe 142 by proximally pushing the tab 196 such as during the blood-aspirating step set forth below. Such a configuration for withdrawing the plunger 176 from the barrel 174 is advantageous when handling the RICC assembly 100 around the coupling hub 144, which is a preferred position for handling the RICC assembly 100 to minimize large movements in a distal-end portion of the RICC 102. Indeed, the more proximal the position in which the RICC assembly 100 is handled, the larger otherwise small, inadvertent movements of the hand will be in the distal-end portion of the RICC 102.

As set forth above, the coupling hub 144 is configured to couple the retractable-needle device 140 and the syringe 142 together such as in the ready-to-deploy state of the RICC assembly 100. The coupling hub 144 includes a carriage connector configured to connect to the coupling hub-connecting portion of the carriage 154, a side arm 180 extending from a side of the coupling hub 144, and a side-arm connector of the side arm 180 configured to connect to the syringe tip 178 of the syringe 142.

The coupling hub 144 is translucent and preferably colorless for observing blood flashback from a venipuncture with the introducer needle 146. Indeed, the coupling hub 144 includes a sealed blood-flashback chamber 182 proximal of a longitudinal through hole of the coupling hub 144 for observing blood flashback. As set forth above, the proximal-end portion of the shaft of the introducer needle 146 including the cutout 149 is disposed in the blood-flashback chamber 182, which cutout 149 is configured to release blood into the blood-flashback chamber 182 upon the needle tip 150 of the introducer needle 146 accessing a blood-vessel lumen of a patient. In addition, the side arm 180 of the coupling hub 144 includes a side-arm lumen that fluidly couples the syringe 142 to the blood-flashback chamber 182 in at least the ready-to-deploy state of the RICC assembly 100. Once blood flashback is observed in the blood-flashback chamber 182 from a venipuncture with the introducer needle 146, the syringe 142 can be used to aspirate additional blood for confirmation of access to the blood-vessel lumen. Seals (e.g., gaskets) at proximal- and distal-end portions of the blood-flash chamber, as well as a seal 184 (e.g., a gasket) about a proximal end of the shaft of the introducer needle 146 through which a bare, unwound portion of the access guidewire 148 passes, enable aspiration of the additional blood with the syringe 142.

The coupling hub 144 can also include a tab 186 in a distal-end portion of the coupling hub 144. The tab 186 is configured to allow a clinician to single handedly advance the RICC 102 over the needle tip 150 with a single finger of a hand while holding a distal-end portion of the retractable-needle device 140 between a thumb and another finger or fingers of the same hand. The tab 186 facilitates a no-touch mechanism for advancing the RICC 102, specifically the distal-end portion of the catheter tube 106, over the needle tip 150, the distal-end portion of the access guidewire 148, or a combination thereof and into a blood-vessel lumen of a patient.

The coupling hub 144 including the side arm 180 thereof can be rigid for holding the syringe 142 in place alongside the retractable-needle device 140 in the RICC assembly 100 in at least the ready-to-deploy state of the RICC assembly 100. That said, the side arm 180 of the foregoing can alternatively be flexible in some embodiments. In such embodiments, the RICC assembly 100 or the introducer 104 thereof includes a clip 198 having a syringe-clipping portion configured to clip the syringe 142 by the barrel 174 thereof and a needle device-clipping portion configured to clip the retractable-needle device 140 by the body-forming housing 158 thereof. The needle device-clipping portion of the clip 198 is configured to allow the retractable-needle device 140 to slide therein. In other words, the retractable-needle device 140 is slidably disposed in the needle device-clipping portion of the clip 198, which allows for the introducer needle-withdrawing step set forth below.

FIGS. 1-4 illustrate the RICC assembly 100 in at least the ready-to-deploy state thereof. When the RICC assembly 100 is in the ready-to-deploy state, little more than the needle tip 150 of the introducer needle 146 extends from the distal end of the RICC 102 for a venipuncture. Indeed, a distal-end portion (e.g., about 7 cm) of the shaft of the introducer needle 146 extends through the longitudinal through hole of the coupling hub 144, through the side aperture 114 of the catheter tube 106, along the introducing lumen 122 of the catheter tube 106, and through the distal end of the RICC 102 when the RICC assembly 100 is in at least the ready-to-deploy state thereof. However, in some embodiments, 1-3 cm or more of the distal-end portion of the shaft can extend from the distal end of the RICC 102 the venipuncture. In such embodiments, the first section 116 of the catheter tube 106 is shorter in length as opposed to the shaft being longer in length. Additional operating states of the number of operating states of the RICC assembly 100 can be discerned from functional aspect of the RICC assembly 100 set forth above or steps of the method for inserting the RICC 102 set forth below.

Methods

A method of the RICC assembly 100 includes a method for inserting the RICC 102 into a blood-vessel lumen of a patient. Such a method includes, in some embodiments, a RICC assembly-obtaining step, a needle tract-establishing step, a RICC-advancing step, and an introducer needle-withdrawing step.

The RICC assembly-obtaining step includes obtaining the RICC assembly 100. As set forth above, the RICC assembly 100 includes the RICC 102 and the introducer 104. The introducer 104 includes the retractable-needle device 140 and the syringe 142 coupled together by the coupling hub 144.

The method can further include a needle tip-ensuring step of ensuring the needle tip 150 of the introducer needle 146 extends from the distal end of the RICC 102 before the needle tract-establishing step. As set forth above, the retractable-needle device 140 includes the introducer needle 146 having the shaft extending through the longitudinal through hole of the coupling hub 144, through the side aperture 114 in the distal-end portion of the catheter tube 106 of the RICC 102, along the introducing lumen 122 of the catheter tube 106, and beyond the distal end of the RICC 102 in at least the ready-to-deploy state of the RICC assembly 100.

The needle tract-establishing step includes establishing a needle tract from an area of skin to the blood-vessel lumen of the patient with the needle tip 150 of the introducer needle 146 while holding the distal-end portion of the retractable-needle device 140. The needle tract-establishing step can also include ensuring blood flashes back into the sealed blood-flashback chamber 182 of the coupling hub 144. As set forth above, the cutout 149 of the shaft of the introducer needle 146 is disposed in the blood-flashback chamber 182 for releasing blood into the blood-flashback chamber 182 upon accessing the blood-vessel lumen of the patient.

The method can further include a blood aspirating-step. The blood aspirating-step includes aspirating blood with the syringe 142 after the needle tract-establishing step but before the introducer needle-withdrawing step. Again, the syringe 142 is fluidly coupled to the blood-flashback chamber 182 of the coupling hub 144 by the side-arm lumen of the side arm 180 for the blood aspirating-step. The blood aspirating-step confirms the needle tip 150 is disposed in the blood-vessel lumen of the patient.

The method can further include an access guidewire-advancing step. The access guidewire-advancing step includes advancing the distal-end portion of the access guidewire 148 from the needle lumen of the introducer needle 146 into the blood-vessel lumen, which facilitates first-stick success by making the access guidewire 148 immediately available before the blood-lumen vessel can be lost due to small inadvertent movements of the RICC assembly 100. The distal-end portion of the access guidewire 148 is advanced, in some embodiments, by distally sliding the slider 172 in the longitudinal slot of the housing 158 of the retractable-needle device 140. As set forth above, the slider 172 can include an extension coupled to the proximal-end portion of the access guidewire 148 disposed in the cavity 156 defined by the housing 158 of the retractable-needle device 140. The access guidewire-advancing step is performed before the first RICC-advancing step such that the distal-end portion of the catheter tube 106 can be advanced over the access guidewire 148 as well as the needle tip 150 of the introducer needle 146.

The first RICC-advancing step includes advancing the distal-end portion of the catheter tube 106 into the blood-vessel lumen over the needle tip 150, the access guidewire 148, or both. As set forth above, the catheter tube 106 includes the first section 116 formed of the first material having the first durometer and the second section 118 formed of the second material having the second durometer less than the first durometer. The first section 116 of the catheter tube 106 is configured with a column strength for advancing the catheter tube 106 into the blood-vessel lumen over the access guidewire 148 or the maneuver guidewire 136 set forth below provided in the maneuver guidewire-advancing step. For example, the first RICC-advancing step can include advancing the catheter tube 106 into the blood-vessel lumen with a single finger of a hand (e.g., with a flick-type motion of the finger) while holding the distal-end portion of the retractable-needle device 140 between a thumb and another finger or fingers of the same hand. The coupling hub 144 includes the tab 186 configured for advancing the catheter tube 106 into the blood-vessel lumen with the single finger. When the coupling is advanced by the single finger, the coupling hub 144, in turn, advances the catheter tube 106 into the blood-vessel lumen.

The introducer needle-withdrawing step includes withdrawing the shaft of the introducer needle 146 from the blood-vessel lumen of the patient, as well as the introducing lumen 122 of the RICC 102 by way of the side aperture 114 of the catheter tube 106. The introducer needle-withdrawing step includes actuating the introducer-needle actuator 152 (e.g., by the button 168) of the retractable-needle device 140. As set forth above, the proximal-end portion of the introducer needle 146 is disposed in the spring-loaded carriage 154 of the retractable-needle device 140, which is configured to thrust proximally into the cavity 156 of the retractable-needle device 140 when the compressed compression spring 160 around the carriage 154 is released by the introducer-needle actuator 152.

The method can further include an access guidewire-withdrawing step of withdrawing the access guidewire 148 from at least the blood-vessel lumen of the patient. The access guidewire-withdrawing step can be performed manually by manual actuation of the access-guidewire actuator 170. For example, the access guidewire 148 can be manually withdrawn from the blood-vessel lumen of the patient by proximally sliding the slider 172 in the longitudinal slot of the housing 158 of the retractable-needle device 140. Alternatively, the access guidewire-withdrawing step can be performed automatically by automatic actuation of the access-guidewire actuator 170. For example, the carriage 154 of the introducer-needle actuating mechanism can be configured to engage the access-guidewire actuator 170 (e.g., the slider 172 or the extension thereof) when the carriage 154 is thrust proximally into the cavity 156 of the retractable-needle device 140 by the compression spring 160. Thus, when the introducer-needle actuator 152 is actuated to release the spring-loaded carriage 154 in the introducer needle-withdrawing step, the access guidewire-withdrawing step is also performed.

Combined, the introducer needle-withdrawing step and the access guidewire-withdrawing step can be considered an introducer-removing step of completely removing the introducer 104 from the RICC 102. Depending upon a length of the access guidewire 148, however, the introducer-removing step can further include separating the introducer 104 from the RICC 102 a distance sufficient to completely withdraw the access guidewire 148 from the introducing lumen 122 of the RICC 102 by way of the side aperture 114 of the catheter tube 106. The introducer-removing step can be performed after the first RICC-advancing step such as after the distal-end portion of the catheter tube 106 is suitably placed within the blood-vessel lumen over both the needle tip 150 and the access guidewire 148.

The method can further a maneuver guidewire-advancing step. The maneuver guidewire-advancing step includes advancing the maneuver guidewire 136 into the blood-vessel lumen by way of, for example, the distal-lumen aperture 130 in the distal end of the RICC 102. As set forth above, the introducing lumen 122 of the catheter tube 106 is coincident with the distal-end portion of the distal lumen 124, particularly the distal-end portion of the distal lumen 124 distal of the side aperture 114. As such, the introducer-removing step of completely removing the introducer 104 from the RICC 102 is mandated before the maneuver guidewire-advancing step to ensure the distal lumen 124, or the introducing lumen 122 thereof, is free of both the introducer needle 146 and the access guidewire 148

The method can further include a second RICC-advancing step of advancing the distal-end portion of the catheter tube 106 farther into the blood-vessel lumen over the maneuver guidewire 136 such as to the SVC. The maneuver guidewire 136 provides the second section 118 of the catheter tube 106 sufficient column strength for the second RICC-advancing step.

The method can further include a sterile barrier-removing step when the sterile barrier is present over the catheter tube 106 between the catheter hub 108 of the RICC 102 and the side aperture 114 of the catheter tube 106. The sterile barrier-removing step includes removing the sterile barrier. The sterile barrier is removed by pulling the sterile-barrier tab of the proximal-end portion of the sterile barrier away from the catheter tube 106 to split the sterile barrier apart.

The method can further include a maneuver guidewire-withdrawing step of withdrawing the maneuver guidewire 136 from the blood-vessel lumen of the patient, as well as completely removing the maneuver guidewire 136 from the RICC 102.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A rapidly insertable central catheter ("RICC") assembly, comprising:
    a RICC including:
        a catheter tube including a side aperture through a side of the catheter tube in a distal-end portion of the catheter tube, the side aperture opening into an introducing lumen of the catheter tube that extends from at least the side aperture to a distal end of the RICC; and
        a catheter hub coupled to a proximal-end portion of the catheter tube; and
        one or more extension legs, each extension leg of the one or more extension legs coupled to the catheter hub by a distal-end portion of the catheter hub;
    an introducer including:
        a retractable-needle device including an introducer needle having a shaft and a needle tip in a distal-end portion of the shaft, a proximal-end portion of the shaft disposed in a carriage of the retractable-needle device; and
        a syringe; and
        a coupling hub coupling the retractable-needle device and the syringe together proximal of the side aperture with the shaft of the introducer needle extending from the carriage, through a sealed blood-flashback chamber of the coupling hub, and out a longitudinal through hole of the coupling hub distal of the blood-flashback chamber such that the needle tip extends beyond the distal end of the RICC when the RICC assembly is in at least a ready-to-deploy state of the RICC assembly.

2. The RICC assembly of claim 1, wherein a cutout of the shaft of the introducer needle is disposed in the blood-flashback chamber, the cutout configured to release blood into the blood-flashback chamber upon the needle tip accessing a blood-vessel lumen of a patient.

3. The RICC assembly of claim 1, wherein the coupling hub includes a side arm extending from a side of the coupling hub, the syringe fluidly coupled to the blood-flashback chamber by a side-arm lumen of the side arm for aspirating blood upon the needle tip accessing a blood-vessel lumen of a patient.

4. The RICC assembly of claim 1, the introducer further including:
    a clip having a syringe-clipping portion and needle device-clipping portion, the syringe-clipping portion of the clip configured to clip the syringe by a barrel of the syringe and the needle device-clipping portion of the clip configured to clip the retractable-needle device by a body of the retractable-needle device while allowing the retractable-needle device to slide in the needle device-clipping portion of the clip.

5. The RICC assembly of claim 4, wherein the syringe includes a plunger disposed in the barrel of the syringe, the plunger including a plunger extension configured to allow a clinician to withdraw the plunger from the barrel by proximally pushing a tab of the plunger extension while handling the RICC assembly around the coupling hub.

6. The RICC assembly of claim 1, wherein the coupling hub includes a tab configured to allow a clinician to single handedly advance the RICC over the needle tip with a single finger of a hand while holding a distal-end portion of the retractable-needle device between a thumb and another finger or fingers of the hand.

7. The RICC assembly of claim 1, the retractable-needle device further including:
    an access guidewire disposed in a needle lumen of the introducer needle; and
    an access-guidewire actuator configured to advance a distal-end portion of the access guidewire beyond the needle tip or withdraw the distal-end portion of the access guidewire into the distal-end portion of the shaft of the introducer needle proximal of the needle tip.

8. The RICC assembly of claim 7, wherein the access-guidewire actuator includes a slider slidably disposed in a longitudinal slot of a housing of the retractable-needle device, the slider including an extension coupled to a proximal-end portion of the access guidewire within a cavity of the retractable-needle device enclosed by the housing.

9. The RICC assembly of claim 8, wherein an introducer-needle actuator of the retractable-needle device is configured to release a compressed compression spring around the carriage when actuated and thrust both the carriage and the introducer needle proximally into the cavity of the retractable-needle device.

10. The RICC assembly of claim 9, wherein the carriage is configured to engage the slider of the access-guidewire actuator when the carriage is thrust proximally into the cavity of the retractable-needle device, thereby withdrawing the access guidewire into the cavity of the retractable-needle device by the distal-end portion thereof together with the introducer needle when the introducer-needle actuator is actuated.

11. The RICC assembly of claim 7, wherein a bare, unwound portion of the access guidewire passes through a seal about a proximal end of the shaft of the introducer needle, thereby enabling aspiration of blood with the syringe upon the needle tip accessing a blood-vessel lumen of a patient.

12. The RICC assembly of claim 1, the RICC further including a sterile barrier over the catheter tube between the catheter hub and the side aperture of the catheter tube, the sterile barrier configured to split apart when a sterile-barrier tab of a proximal-end portion of the sterile barrier is pulled away from the catheter tube by the sterile-barrier tab.

13. The RICC assembly of claim 1, wherein the RICC includes a set of three lumens including a distal lumen, a medial lumen, and a proximal lumen formed of fluidly connected portions of three catheter-tube lumens, three hub lumens, and three extension-leg lumens, the introducing lumen of the catheter tube coincident with a distal-end portion of the distal lumen, and wherein the distal lumen has a distal-lumen aperture in the distal end of the RICC, the medial lumen has a medial-lumen aperture in the side of the catheter tube proximal of the distal-lumen aperture, the proximal lumen has a proximal-lumen aperture in the side of the catheter tube proximal of the medial-lumen aperture, and the side aperture of the catheter tube is between the distal-lumen aperture and the medial-lumen aperture, between the medial-lumen aperture and the proximal-lumen aperture, or proximal of the proximal-lumen aperture.

14. The RICC assembly of claim 1, wherein the blood-flashback chamber includes a seal in a proximal-end portion of the blood-flashback chamber and another seal in a distal-end portion of the blood-flashback chamber.

15. A method for inserting a rapidly insertable central catheter ("RICC) into a blood-vessel lumen of a patient, comprising:
    obtaining a RICC assembly including the RICC and an introducer of a retractable-needle device and a syringe coupled together by a coupling hub, the retractable-needle device including an introducer needle having a shaft extending from a carriage of the retractable-needle device, through a sealed blood-flashback chamber of the coupling hub, and out a longitudinal through hole of the coupling hub distal of the blood-flashback chamber, through a side aperture in a distal-end portion of a catheter tube of the RICC, along an introducing lumen of the catheter tube, and beyond a distal end of the RICC in at least a ready-to-deploy state of the RICC assembly;
    establishing a needle tract from an area of skin to the blood-vessel lumen of the patient with a needle tip of the introducer needle while holding a distal-end portion of the retractable-needle device;
    advancing a distal-end portion of the catheter tube into the blood-vessel lumen over the needle tip; and
    withdrawing the shaft of the introducer needle from the introducing lumen by way of the side aperture of the catheter tube.

16. The method of claim 15, wherein establishing the needle tract includes ensuring blood flashes back into the blood-flashback chamber of the coupling hub, a cutout of the shaft of the introducer needle disposed in the blood-flashback chamber between seals at proximal- and distal-end portions of the blood-flashback chamber for releasing blood into the blood-flashback chamber upon establishing the needle tract.

17. The method of claim 16, further comprising aspirating blood with the syringe before withdrawing the shaft of the introducer needle from the introducing lumen, thereby confirming the needle tip is disposed in the blood-vessel lumen of the patient, the syringe fluidly coupled to the blood-flashback chamber by a side-arm lumen of a side arm of the coupling hub for aspirating blood upon accessing the blood-vessel lumen of the patient.

18. The method of claim 15, wherein advancing the distal-end portion of the catheter tube into the blood-vessel lumen includes advancing the catheter tube into the blood-vessel lumen with a single finger of a hand while holding a distal-end portion of the retractable-needle device between a thumb and another finger or fingers of the hand, the coupling hub including a tab configured for advancing the catheter tube into the blood-vessel lumen with the single finger.

19. The method of claim 15, further comprising advancing a distal-end portion of an access guidewire disposed in a needle lumen of the introducer needle into the blood-vessel lumen before advancing the distal-end portion of the catheter tube into the blood-vessel lumen over the needle tip, the advancing step including sliding a slider slidably disposed in a longitudinal slot of a housing of the retractable-needle device, which slider includes an extension coupled to a proximal-end portion of the access guidewire disposed in a cavity of the retractable-needle device enclosed by the housing.

20. The method of claim 19, wherein withdrawing the shaft of the introducer needle from the introducing lumen of the catheter tube includes actuating an introducer-needle actuator of the retractable-needle device, a proximal-end portion of the introducer needle disposed in the carriage of the retractable-needle device configured to thrust proximally into the cavity of the retractable-needle device when a compressed compression spring around the carriage is released by the introducer-needle actuator.

21. The method of claim 15, further comprising advancing a maneuver guidewire into the blood-vessel lumen by way of a distal lumen having a distal-lumen aperture in the distal end of the RICC, the introducing lumen of the catheter tube coincident with a distal-end portion of the distal lumen, thereby mandating withdrawing the shaft of the introducer needle from the introducing lumen of the catheter tube before advancing the maneuver guidewire into the blood-vessel lumen.

22. The method of claim 15, further comprising removing a sterile barrier disposed over the catheter tube between a catheter hub of the RICC and the side aperture of the catheter tube by pulling a sterile-barrier tab of a proximal-end portion of the sterile barrier away from the catheter tube to split the sterile barrier apart.

23. A rapidly insertable central catheter ("RICC") assembly, comprising:
    a RICC including a catheter tube having a side aperture through a side of the catheter tube in a distal-end portion thereof, the side aperture opening into an introducing lumen of the catheter tube that extends from at least the side aperture to a distal end of the RICC;
    an introducer including:
        a retractable-needle device including an introducer needle having a shaft, a cutout of the shaft, and a needle tip in a distal-end portion of the shaft, a proximal-end portion of the shaft disposed in a carriage of the retractable-needle device; and
        a syringe; and
    a coupling hub including:
        a side arm;
        a sealed blood-flashback chamber having a seal in a proximal-end portion of the blood-flashback chamber and another seal in a distal-end portion of the blood-flashback chamber; and
        a longitudinal through hole distal of the blood-flashback chamber, the coupling hub coupling the retractable-needle device and the syringe together proximal of the side aperture in at least a ready-to-deploy state of the RICC assembly, in which:
            the shaft of the introducer needle extends from the carriage, through the blood-flashback chamber of the coupling hub, out the longitudinal through hole of the coupling hub, and through the introducing lumen of the catheter tube such that the needle tip extends beyond the distal end of the RICC;
            the cutout of the shaft is disposed in the blood-flashback chamber for releasing blood into the blood-flashback chamber upon the needle tip accessing a blood-vessel lumen of a patient; and
            the syringe is fluidly coupled to the blood-flashback chamber by a side-arm lumen of the side arm for aspirating blood through the blood-flashback chamber upon accessing the blood-vessel lumen.

\* \* \* \* \*